(12) United States Patent
Riley et al.

(10) Patent No.: US 7,183,319 B2
(45) Date of Patent: Feb. 27, 2007

(54) PHENYLETHYLAMINE DERIVATIVES AND THEIR USE IN THE TREATMENT OF MELANOMA

(76) Inventors: Patrick Anthony Riley, 2 The Grange, Grange Avenue, London (GB) N20 8AB; Andrew Photiou, 68 St. Augustines Road, London (GB) NW1 9RP; Tariq Hussain Khan, 36 Southmill Road, Bishop Stortford, Hertfordshire (GB) CM23 3DP; Helen Mary Isted Osborn, 36 Southmill Road, Bishop Stortford, Hertfordshire (GB) CM23 3DP; Hugh Malkin, 1 Upland Court, 33 London Road, Forest Hill, London (GB)

( * ) Notice: Subject to any disclaimer, the term of this patent is extended or adjusted under 35 U.S.C. 154(b) by 281 days.

(21) Appl. No.: 10/333,933

(22) PCT Filed: Jul. 25, 2001

(86) PCT No.: PCT/GB01/03339

§ 371 (c)(1),
(2), (4) Date: Jul. 17, 2003

(87) PCT Pub. No.: WO02/08174

PCT Pub. Date: Jan. 31, 2002

(65) Prior Publication Data

US 2004/0029967 A1  Feb. 12, 2004

(30) Foreign Application Priority Data

Jul. 26, 2000 (GB) .................................. 0018376.4
Nov. 10, 2000 (GB) .................................. 0027574.3

(51) Int. Cl.
*A01N 37/12* (2006.01)
*A01N 37/44* (2006.01)

(52) U.S. Cl. ...................... 514/563; 514/575; 514/617; 562/621; 564/161

(58) Field of Classification Search ................ 514/563, 514/575, 617; 562/621; 564/161
See application file for complete search history.

(56) References Cited

U.S. PATENT DOCUMENTS 4,115,539 A   9/1978 Eisenhardt, Jr. et al.
5,958,971 A * 9/1999 Burke et al. ................. 514/476

FOREIGN PATENT DOCUMENTS

EP    0 584 552 A2 *  3/1994
WO   WO 98/25886    *  6/1998

OTHER PUBLICATIONS

Hong et al. *Synthesis and Biological Activity of Analogs of Naturally Occuring 6-Ureidopurines and Their Nucleosides*, Journal of Medicinal Chemistry (1973) vol. 16, No. 2, pp. 139-147.

* cited by examiner

*Primary Examiner*—Johann Richter
*Assistant Examiner*—Chukwuma Nwaonicha
(74) *Attorney, Agent, or Firm*—Hodgson Russ LLP

(57) ABSTRACT

Novel mono- and dihydroxy phenylethylamine derivatives useful in treating melanoma are provided having the formulae (Ia, Ib or Ic). In the above formulae, $R^a$ is hydrogen or —$COOR^b$, $R^b$ is hydrogen or $C_{1-6}$ alkyl; $R^e$ and $R^e$ independently represent hydrogen and hydroxy, $R^f$ is hydrogen, $C_{1-4}$ alkyl or halogen, X is —CHOH—, —$CH_2$-oxygen or sulphur, m is zero or 1, W is oxygen or sulphur, and —ODrug, —NHDrug and —N(Drug)$_2$ each represent a residue of a therapeutically active agent. The above compounds are prodrugs which are inactive until metabolised by enzymes expressed by host melanoma cells. The invention allows a greater amount of active agent to be used while reducing systemic side effects

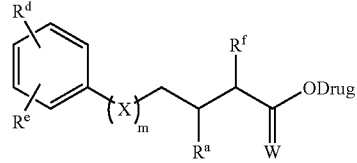
(Ia)

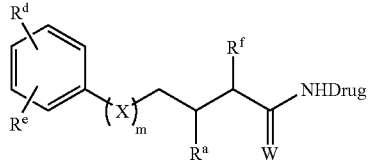

(Ib)

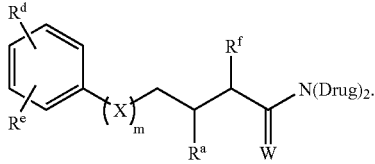

(Ic)

7 Claims, 1 Drawing Sheet

PHENYLETHYLAMINE DERIVATIVES AND THEIR USE IN THE TREATMENT OF MELANOMA

BACKGROUND TO THE INVENTION

Figure 1:
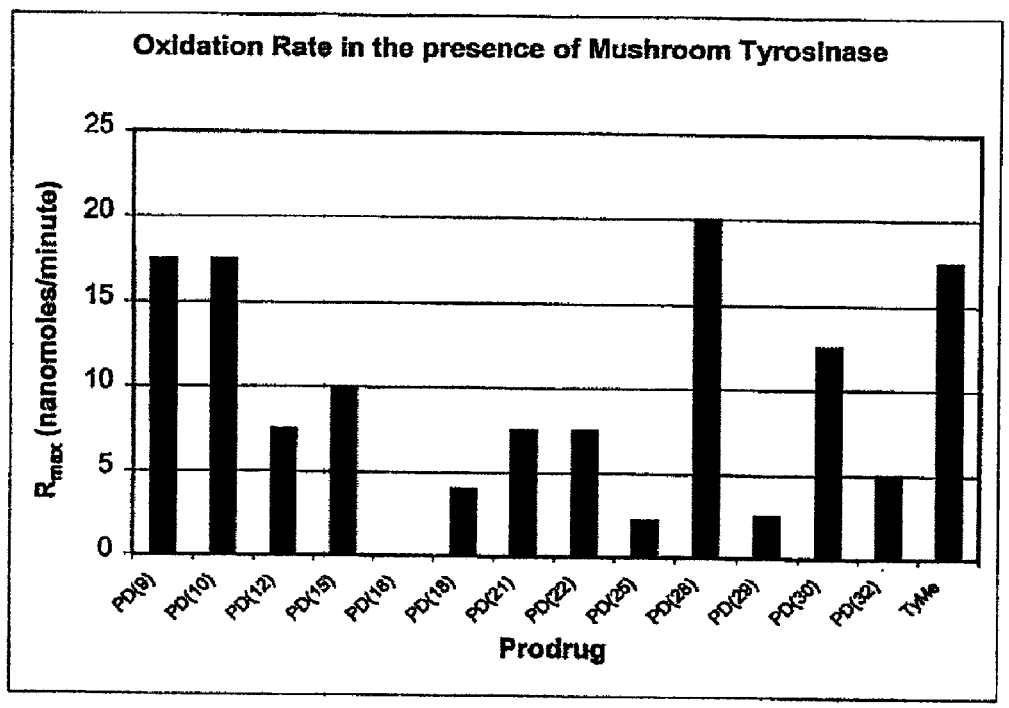

It has recently been shown that tumours may be treated selectively through the use of prodrugs, these prodrugs being inactive until metabolised by enzymes expressed by the host. This method of treating cancers is promising, as it allows a greater amount of active agent to be used while reducing systemic side effects.

This type of treatment has been proposed as having potential for the treatment of malignant melanoma, in particular when utilising prodrugs which are effectively recognised by the enzyme tyrosinase. When tyrosinase acts upon the prodrug, an active antitumour agent is released.

In adults, tyrosinase is specifically produced in melanocytes, cells which are responsible for pigmentation. When a patient suffers from melanoma the cancerous cells display a heightened level of tyrosinase. Thus, by employing a prodrug which is specifically recognised by tyrosinase, the prodrug can show greater selectivity for the cancerous cells.

Thus, our International Application No. PCT/GB97/03433 discloses novel prodrugs and assay reagents which are useful as therapeutic agents. These prodrugs and assay reagents were described as being substrates for tyrosinase and of being capable of releasing a therapeutically active agent at a desired location. In particular, a compound called "Prodrug A" is disclosed. Prodrug A has certain drawbacks that make it less than ideal as viable drug for use in the treatment of melanoma. Thus, Prodrug A, although being a substrate for tyrosinase, is also a substrate for other enzymes present in the body. Furthermore, tests have shown Prodrug A to be relatively unstable in solution.

Hong et al. in *Journal of Medicinal Chemistry*, 1973, Vol. 16, No. 2, p139–147 disclose naturally-occurring 6-ureidopurines and the nucleosides. These compounds show cytokinin and growth inhibitory activity, but have not been shown to have activity on melanoma cells.

U.S. Pat. No. 4,115,539 relates to tyrosine derivatives which may be coupled with other compounds to form derivatives receptive to tagging, e.g. by radiolabeling. The derivatives are useful in detecting compounds of interest in nano- or even pico-molar amounts. In one such compound, tyrosine is coupled to digoxin via a carbamate linker. The disclosed compounds are stated to be useful in analysis techniques, but are not disclosed to have any therapeutic applications, far less to be potential candidates for prodrug treatment of melanoma.

European Application No. 0 583 552 relates to conjugates of chlorophyll and bacteriochlorophyll which are useful as photosensitizers in the diagnosis and therapy of tumours. The chlorophyll and bacteriochlorophyll moieties are conjugated with cell-specific ligands such as hormones, growth factors or tumour-specific antibodies to facilitate targeting the tumour site.

It is an aim of the present invention to provide improved prodrugs for use in the treatment of melanoma. It is a further object of the invention to provide prodrugs which avoid problems associated with prior art prodrugs, specifically which show improved stability and increased selectivity. Thus, it has been found that compared to Prodrug A, compounds which incorporate a urea linkage are advantageous. Prodrug A has a carbamate linkage between the therapeutically active entity and the entity that is recognised by the tyrosinase enzyme. Further, a class of compounds which have only a single hydroxy substituent in the para position have been found to be excellent substrates for tyrosinase enzymes, and to have high specificity.

SUMMARY OF THE INVENTION

According to one aspect of the invention, there are provided compounds having the formula (Ia), (Ib) or (Ic), or a pharmaceutically acceptable salt thereof:

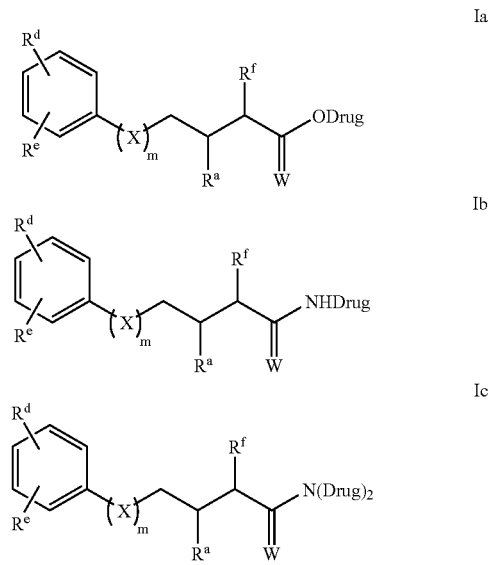

wherein $R^a$ is hydrogen or —$COOR^b$, $R^b$ is hydrogen or $C_{1-6}$ alkyl; $R^d$ and $R^e$ independently represent hydrogen and hydroxy, $R^f$ is hydrogen, $C_{1-4}$ alkyl or halogen, X is —CHOH—, —$CH_2$— oxygen or sulphur, m is zero or 1, W is oxygen or sulphur, and —ODrug, —NHDrug and —N(Drug)$_2$ each represent a residue of a therapeutically active agent with the provisos (1) that where said compound has general formula (Ia) wherein m is 0, W represents oxygen $R^d$ is hydrogen and $R^e$ is hydroxyl in the para position, and $R^a$ represents —COOMe, —ODrug does not represent a residue of digoxin, and (2) that where said compound has general formula (Ib) wherein m is zero, W represents oxygen and $R^d$ is hydrogen, $R^e$ is hydroxyl in the para position.

According to a preferred aspect one of the invention, there are provided compounds having the formulas (IIa), (IIb) or (IIc) or pharmaceutically acceptable salts thereof:

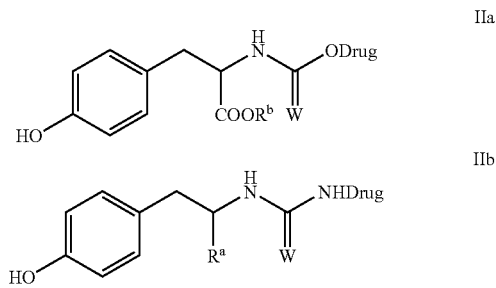

-continued

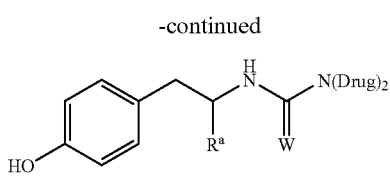

IIc wherein $R^a$ is hydrogen or —COOR$^b$, and $R^b$ is hydrogen or $C_{1-6}$ alkyl; W is oxygen or sulphur, and —ODrug, —NH-Drug and —N(Drug)$_2$ represent a residue of a therapeutically active agent, with the proviso that where said compound has general formula (Ia) and $R^b$ represents methyl, —ODrug does not represent a residue of digoxin.

The invention also compounds having the general formulae (IIIa) and (IIIb) or pharmaceutically acceptable salts thereof.

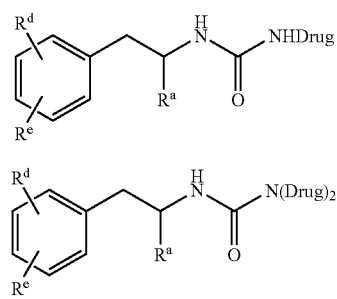

wherein $R^a$ is hydrogen or —COOR$^b$, and $R^b$ is hydrogen or $C_{1-6}$ alkyl; —NHDrug and —N(Drug)$_2$ represent a residue of a therapeutically active agent; and $R^d$ and $R^e$ independently represent hydrogen or hydroxy.

In a preferred embodiments of compounds of Formulae Ia, Ib, Ic, IIIa and IIIb, only one of $R^d$ and $R^e$ is hydrogen, with the remaining positions on the phenyl ring remaining unsubstituted. It is particularly preferable for the single hydroxy group to be present in the para position.

Further preferred classes of compounds of the invention are wherein:
$R^b$ is hydrogen;
$R^b$ is methyl;
$R^a$ is hydrogen;
W represents oxygen.

It will be appreciated that compounds of the invention can form pharmaceutically acceptable salts, such as acid addition salts. Examples of suitable acids for salt formation include hydrochloric, sulfuric, phosphoric, acetic, citric, oxalic, malonic, salicylic, malic, fumaric, succinic, ascorbic, maleic, methanesulfonic and other mineral and carboxylic acids well known in the art.

Methods of preparation of acid addition salts will be apparent to those skilled in the art. For example, the salts may be prepared by contacting the free base form with a sufficient amount of the desired acid to produce a salt in the conventional manner. The free base forms may be regenerated by treating the salt with a suitabl dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the acid and base forms are otherwise equivalent to their respective free base forms for the purposes of the invention.

All such acid and base salts are intended to be pharmaceutically acceptable salts within the scope of the invention and all acid and base salts are considered equivalent to the free forms of the corresponding compounds for the purposes of the invention.

The compounds of the invention may preferably be derived from the class of therapeutically active agents termed "mustards". Such compounds typically contain haloalkylamine e.g. bis(chloroethyl)amine groups. Mustards are able to act as intercalating agents, and cross-link strands of DNA. In order to do so, the nitrogen lone pair first causes a chloride ion to leave, forming a three-membered ring containing a tertiary nitrogen atom. DNA then acts as a nucleophile, opening the ring and forming an entity believed to incorporate the structure:

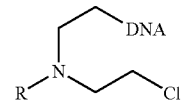

This process is repeated, with the result being that the mustard acts as a "claw", reacting with the DNA at two points (one on each strand), and preventing the division of the DNA.

The compounds of the invention in this category (mustards) may contain —NHDrug, —ODrug and —N(Drug)$_2$ groups represented by the formulae:

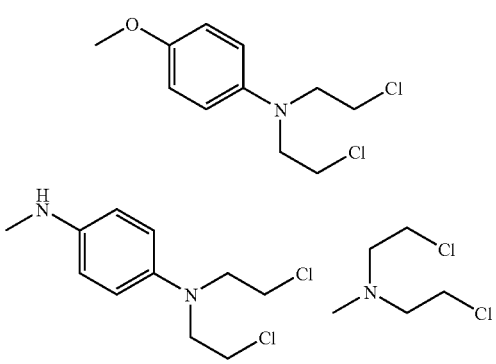

Particularly preferred compounds of the invention have the following formulae, known as "UPD", "2.1.1" and "1.1.2" respectively:

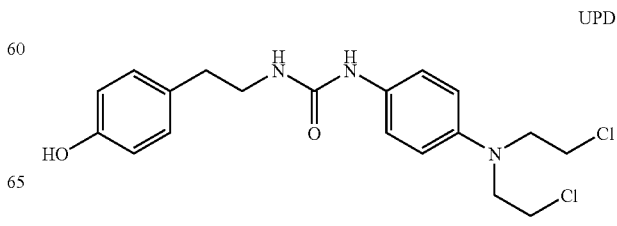

UPD

-continued

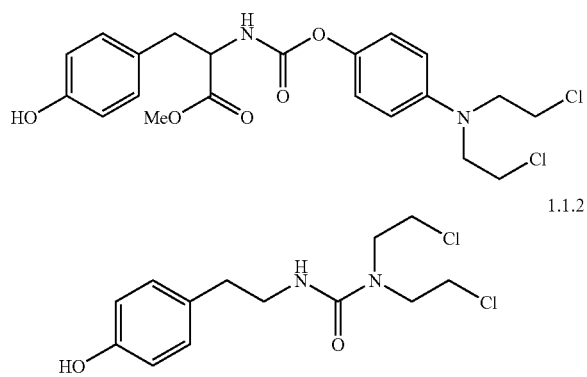

Other examples of compounds according to the invention have residues of taxol, gemcitabine or daunomycin in place of mustard groups discussed above. Thus the residue of the therapeutically active agent may preferably be selected from —O(Taxol), —O(Gemcitabine) and —NH(Daunomycin).

It is further within the scope of the invention to provide the use of compounds having the general formula Ia, Ib, Ic, IIa and IIb in the manufacture of pharmaceutical compositions for the treatment of melanoma.

Such pharmaceutical compositions may include any of the customary excipients used in formulating dosage forms. Suitable dosage forms include tablets, capsules, coated pills, injectable solutions and suspensions.

GENERAL SYNTHETIC METHODS

The following section described general synthetic procedures for producing compounds according to the invention.

Synthesis of Phenyl Mustard Prodrugs

The general protocol for the synthesis of the various prodrugs was based on the premise of forming a reactive carbonate that was prone to nucleophilic attack by a primary or secondary amine. Prodrugs with a carbamate linkage were synthesised as previously reported[1], and required access to the reactive carbonate intermediate 6. Facile preparation of p-hydroxyphenyl mustard hydrochloride 5 was achieved by treating benzyloxyaniline 2 with ethylene oxide to give diol 3.[2] Conversion to the bis-chloroethyl amino compound 4 was facilitated using methane sulfonyl in anhydrous pyridine.[3] Subsequent formation of the hydrochloride salt and benzyl cleavage by hydrogenation gave the desired p-hydroxyphenyl mustard hydrochloride 5. Preparation of the carbonate 6, ready for coupling with primary and secondary amines, was achieved by heating 5 at reflux in toluene in the presence of p-nitrophenyl chloroformate (Scheme 2).

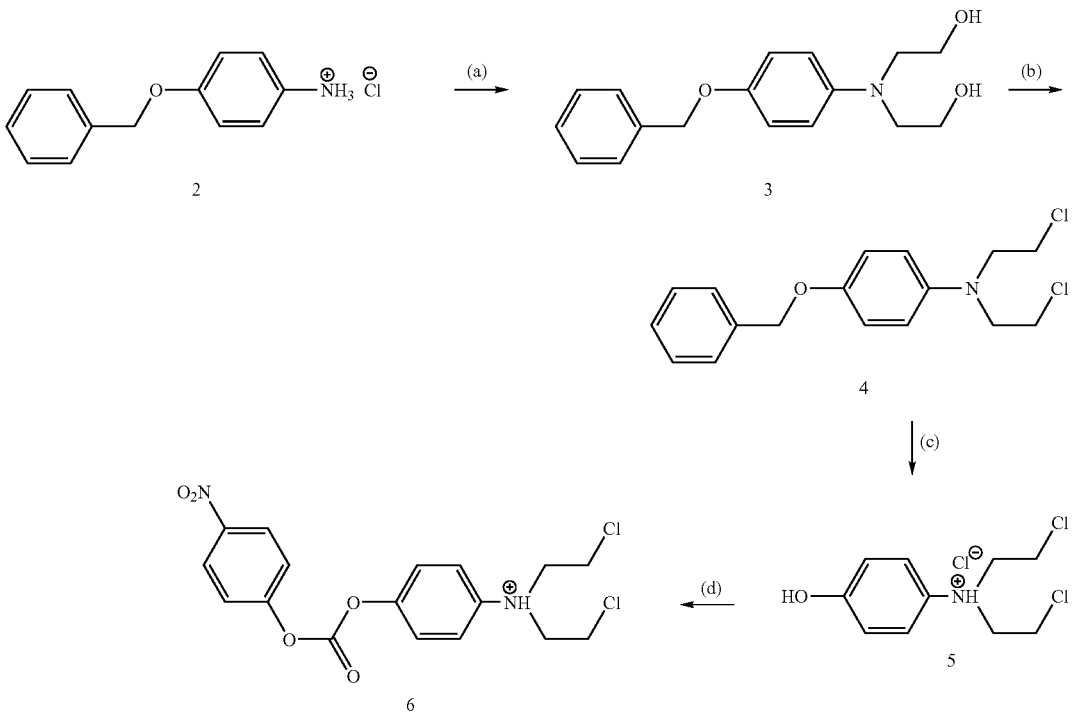

Scheme 2: synthesis of the reactive carbonate 6. Reagents: (a) triethylamine, ethylene oxide, 88%, (b) mesyl chloride, pyridine, 59%, (c) $HCl_{(g)}$ then $H_2$ Pd/C, 51%, (d) p-nitrophenylchloroformat, triethylamine, 64%.

Coupling of carbonate 6 with various primary amines proceeded smoothly in anhydrous dimethylformamide to give the corresponding prodrugs in good to excellent yield (Table 1).

tive was also prepared. Initial attempts at functional group interconversion, using Lawesson's reagent[4] were disappointing, and consequently an alternative synthesis was adopted.

TABLE 1 phenyl mustard prodrugs afforded from the reaction between various amines and carbonat 6.

| Entry | Amine | Carbonate | Prodrug | Yield |
|---|---|---|---|---|
| 1 | (7) R = H<br>(8) R = OH | (6) | (9) R = H<br>(10) R = OH | (9) 47%<br>(10) 73% |
| 2 | (11) | (6) | (12) | 62% |
| 3 | (13) R = H<br>(14) R = CO$_2$Me | (6) | (15) R = H<br>(16) R = CO$_2$Me | (15) 52%<br>(16) 54% |
| 4 | (17) | (6) | (18) | 44% |
| 5 | (19) X = O<br>(20) X = S | (6) | (21) X = O<br>(22) X = S | (21) 27%<br>(22) 39% |

Since prodrug 12 was derived from an excellent tyrosinase substrate, tyrosine methyl ester, a thiocarbonate derivative p-Hydroxyphenyl hydrochloride mustard 5 was treated with pentafluorophenylchlorothionoformate 23 to give thiocarbonate 24, which was converted to prodrug 25 by treatment with tyrosine methyl ester (Scheme 3).

Scheme 3:
synthesis of thiocarbonate linked prodrug 25.

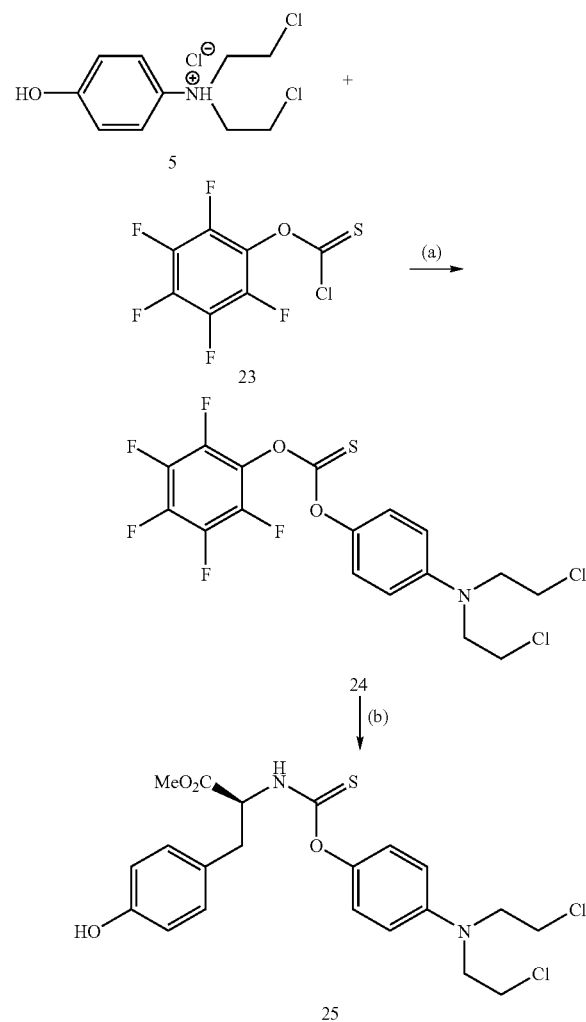

Reagents: (a) triethylamine, toluene, (b) tyrosine methyl ester, dimethylsulfoxide, $N_2$, 68% (overall yield).

Synthesis of bis-(2-chloroethyl)amine Urea Mustards

For this series of prodrugs two synthetic approaches were examined. The initial protocol mirrored that used for the formation of the phenol mustard prodrugs and involved the synthesis of the p-nitrophenol carbamate 27 (Scheme 4).

Scheme 4:
synthesis of bis-chloroethyl amine urea linked mustards.

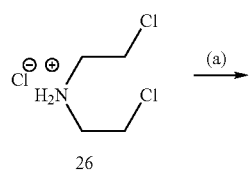

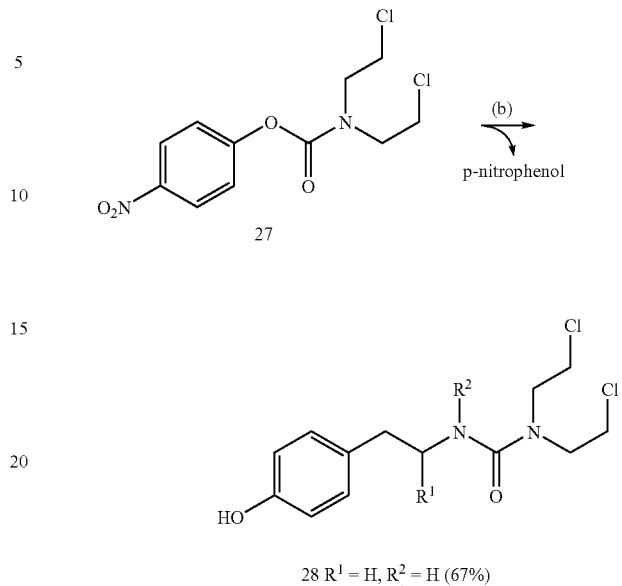

28 $R^1$ = H, $R^2$ = H (67%)
29 $R^1$ = H, $R^2$ = Me (18%)
30 $R^1$ = $CO_2Me$, $R^2$ = H (60%)

Reagents: (a) triethylamin, dimethylformamide, p-nitrophenylchloroformate, 70%.
(b) amine 7, 11 or N-methyl tyramine, reflux, $N_2$.

Synthesis of the p-nitrophenyl carbamate 27 was easily achieved by reacting p-nitrophenyl chloroformate with bis-(2-chloroethyl)amine hydrochloride 26. Mustard 27 was then coupled to primary and secondary amines as before (Scheme 5). In thes cases, the p-nitrophenol by-product had to be removed from the prodrugs using silica gel column chromatography.

In addition, with the aim of minimising purification procedures, two one-pot methodologies were developed. The one-pot strategies relied upon in situ formation of a reactive intermediate which, upon reaction with a primary or secondary amin, would afford the prodrug together with a volatile by-product. The one-pot rationale and formation of prodrugs 28–30 can be seen in scheme 5.

Scheme 5:
One pot synthesis of bis-chloroethyl amine urea linked mustards.

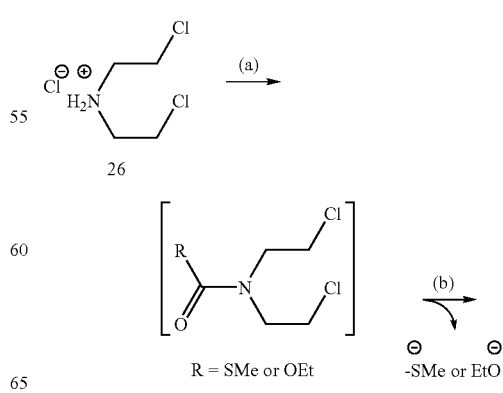

-continued

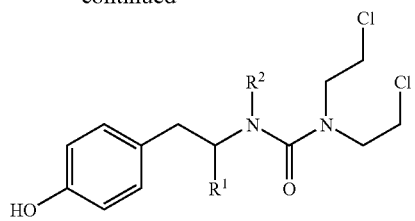

28 R¹ = H, R² = H (R = SMe 84%, OEt 71%)
29 R¹ = H, R² = Me (R = SMe 23%, OEt 20%)
30 R¹ = CO₂Me, R² = H (R = SMe 78%, OEt 75%)

Reagents: (a) triethylamine, dimethylformamide, ethyl chloroformate or methyl chlorothioformate. (b) amine 7, 11 or N-methyl tyramine, reflux.

In all cases, the one-pot approach afforded higher yields than employing the p-nitrophenylchloroformate method. Therefore, when combined with easier purification, the one pot approach is, without doubt, a superior method for prodrug synthesis.

The final class of compounds synthesised and tested by oximetry were th daunomycin-based prodrugs. These were easily obtained using a similar two pot reaction scheme, via the reactive carbamate 31. Addition of daunomycin then afforded the urea linked prodrug 32 (Scheme 6).

Scheme 6:
synthesis of daunomycin prodrug 32.

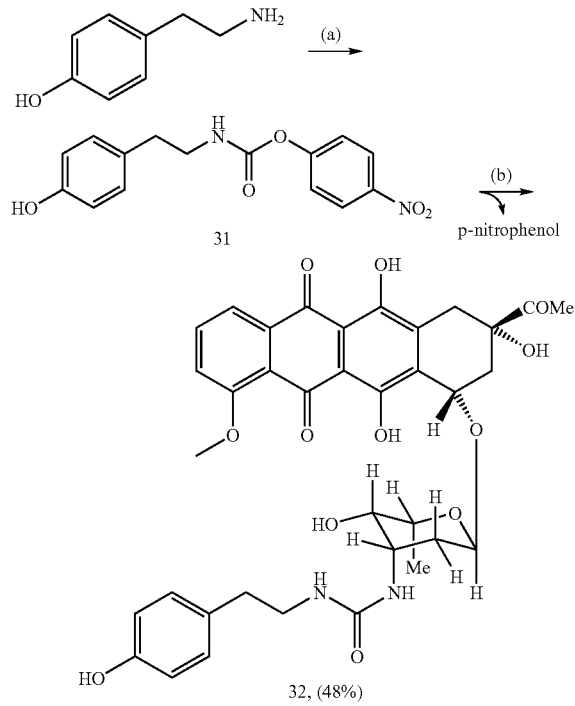

Reagents: (a) p-nitrophenylchloroformate, dichloromethane, reflux.
(b) daunomycin, N,N-diisopropylethylamine, dimethylformamide.

EXAMPLES

The synthesis of preferred compounds of the invention is illustrated in the following examples.

General Experimental

All NMR spectra were recorded on a Bruker WM250, Bruker AC250, Bruker Avance DPX 250, Bruker AMX400 or Jeol AX400 spectrometer, using $CHCl_3$ as an internal standard unless stated otherwise (7.26 ppm for $^1$H NMR, 77.0 ppm for $^{13}$C NMR). $^{13}$C spectra were recorded using Distortionless Enhancement by Polarisation Transfer. Mass spectra were recorded on a Fisons VG Autospec. Infra red spectra were recorded on a Perkin-Elmer Paragon 1000 F.T.-I.R. spectrometer. Optical activities were determined using a Perkin-Elmer 341 polarimeter. Melting points were determined using an Electrothemal digital melting point apparatus, and are uncorrected. Scanning oximetry was performed using a YSI model 5300 biological oxygen monitor.

Unless stated otherwise, all chemicals and materials were obtained from the Sigma-Aldrich Chemical Company, the B.D.H. Merk Chemical Company or Lancaster Chemicals and were, used as received. Silica gel for column chromatography was obtained from Merck, with a pore diameter of 6 nm. Alumina column chromatography was performed using 150 mesh neutral aluminium oxide, obtained from the Aldrich Chemical Company. Silica and alumina thin layer chromatography was performed on pre-coated aluminium sheets, with a 0.2 mm thickness. Anhydrous solvents were purchased and used as received. Mushroom tyrosinase (3,520 units/mg) was used at a concentration of 300 units/mL in 0.1 M phosphate buffered saline (pH 7.4).

Example 1

Synthesis of UPD (4-di(2-chloroethyl)aminoanilino-4-hydroxyphenethylamino-methanone)

UPD was synthesised by the procedure shown in Scheme 1. Tyramine (101) (10 g, 73 mmol), and nitrophenyl isocyanate (102) (11.98 g, 73 mmol) were dissolved in anhydrous pyridine (5 mL) and stirred at room temperature for 6 hours. The mixture was concentrated under vacuum (residual Py azetroped using toluene) to give 4-hydroxyphenethylamino4-nitroanilinmethanone (103) in quantitative yield by TLC ($CH_2Cl_2$) and $^1$H NMR.

(103) (10 g, 36.9 mmol), was dissolved in hot abs EtOH (250 mL) and allowed to cool before 5 mol % of 10% Pd on carbon was added. The flask was evacuated and $H_2$ was introduced under atmospheric pressure. The mixture was stirred for 12 hours, filtered through celite and concentrated under vacuum to give 4-aminoanilino-4-hydroxyphenethyl-aminomethanone (104) as an off-white solid in 100% yield.

(104) (5 g, 18,42 mmol) was dissolved in a solution of $H_2O$/MeOH/conc. AcOH (100 mL/10 mL/10 mL) and stirred at room temperature. To this solution cold ethylene oxide (10 mol/eq) was added slowly. The mixture was stirred at room temperature for 6 hours, and a further 10 mol/eq of ethylene oxide was added. This was repeated until an off-white precipitate formed. The precipitate was filtered off and recrystallised (hot EtOAc) to give 4-di(hydroxyethyl)aminoalinino-4-hydroxyphenethyl-aminomethanone (105) as an off-white solid (70% yield).

(105) (2.8 g, 7.8 mmol), $CH_2Cl_2$ (4 mL), pyridine (6 mL) were cooled and thionyl chloride (2.64 mL) was added. The mixture was heated at reflux for 1 hour, allowed to cool and diluted with $CH_2Cl_2$ (200 mL). The mixture was washed with water (2×200 mL), th organics were dried over $MgSO_4$ and reduced under vacuum to give a brown oily solid (see compound 106 (as identified by $^1$H NMR and MS)).

The oily solid was then taken up in hot EtOAc/Ether (100 mL/100 mL) and allowed to cool. Once cool, HCl gas was passed through the solution to give an off-white precipitate. The precipitate was filtered off and concentrated under vacuum to give (UPD) as a light brown honeycomb solid, which was recrystallised (hot EtOAc) to afford >99.5 purity by HPLC.

Example 2

Synthesis of 1.1.2 (bis-(2-chloroethyl)amino-4-hydroxyphenylamino-methanone): One Pot Method The synthesis of 1.1.2 is shown in Scheme 2. Bis-(2-Chloroethyl)amine hydrochlorid (107) (200 mg, 1.1 mmol) was dissolved in dichloromethane (15 mL), and triethylamine (0.45 mL, 3,3 mmol) was added. The mixture was stirred for 5 minutes at ambient temperature and ethyl chloroformate (108) or methyl chlorothioformate (1.32 mmol) was added. The mixture was stirred until no bis-(2-chloroethyl)amine remained by TLC (ethyl acetate) (109).

Tyramine (110) (300 mg, 2,2 mmol) was added and the mixture was heated und r reflux for 4 hours. The mixture was allowed to cool, purified by dry flash column chromatography (silica gel, dichloromethane 200 $cm^3$) and concentrated in vacuo to yield prodrug 1.1.2 as an orange/brown oil (234 mg, 67% for methyl chlorothioformate and 229 mg, 64% for ethyl chloroformate).

Example 3

Synthesis of 2.1.1 ((R)-[2'-amin-3-(4"-hydroxyphenyl)propionic acid methyl ester]-carbamic acid p-(bis-2-chloroethylamino) ph nyl est r)

2.1.1 was synthesised by the following procedure, as shown in Scheme 3. 4-benzyloxyaniline hydrobromide (111) (11.8 g, 0.05 mol) was suspended in glacial acetic acid (70 $cm^3$) and water (70 $cm^3$) and cooled to 0° C. Ethylene oxide (17.64 g, 20 $cm^3$, 0.4 mol) was then added, in 1 $cm^3$ portions, the solution allowed to warm to room temperature and stirred until no starting material remained by TLC. Additional ethylene oxide was added as required in order to drive the reaction to completion. After this time, the solution was concentrated in vacuo (T<60° C.) to give a red/brown syrup, which was re-dissolved in chloroform (100 $cm^3$). This solution was washed with water (50 $cm^3$) and saturated sodium bicarbonate solution (50 $cm^3$), dried (magnesium sulfate), filtered and concentrated in vacuo. Recrystallisation (toluene/hexane) gave the diol Benzyl-p-(bis-2-hydroxyethylamino) phenyl ether (112) as a pale cream powder (12.55 g, 88%).

Phosphorous Pentachloride Method:

(112) (5.8 g, 0.02 mol) was dissolved in chloroform (30 $cm^3$) and cooled to 0° C. Phosphorous pentachloride (12.5 g, 0.06 mol) was slowly added, the mixture warmed to room temperature and left to stand overnight. The resultant black mixture was then refluxed for one hour, after which time it was cooled to room temperature, poured onto crushed ice (20 $cm^3$), stirred vigorously and poured onto an additional portion of crushed ice (20 $cm^3$). The organic layers were separated, washed with saturated bicarbonate solution (2×50 $cm^3$) and dried (magnesium sulfate). After filtration and concentration in vacuo, the resultant black oil was purified by eluting through a short pad of silica with dichloromethane. Recrystallisation (dichloromethane:hexane) gave the dichloride, benzyl-p-(bis-2-chloroethylamino)phenyl ether (113), as white plates (3.33 g, 52%).

Mesyl Chloride Method:

(112) (2.0 g, 7.2 mmol) was dissolved in anhydrous pyridine (11 $cm^3$) and cooled to 0° C. Mesyl chloride (28.8 mmol, 2.23 $cm^3$) was added and the solution stirred at 2–4° C. for 20 minutes, followed by heating at 80° C. for 30 minutes. Ethyl acetate (30 $cm^3$) and wat r (30 $cm^3$) were then added, the organic fraction collected, dried (magnesium sulfate), filtered and concentrated in vacuo. Column chromatography (silica, dichloromethane) gave the dichloride (113) (1.38 g, 59%) as a white powder.

Hydrogen chloride gas was bubbled through a solution of (113) (3.3 g, 0.01 mol) in methanol (35 $cm^3$), until complete dissolution occurred.

Filtration and concentration in vacuo gave the hydrochloride salt as a white powder, which was immediately re-suspended in ethanol (40 $cm^3$) containing 10% palladium on carbon (0.17 g). The suspension was stirred under an atmosphere of hydrogen until no starting material remained (TLC). The suspension was then filtered over celite and concentrated in vacuo to give p-(bis-2-chloroethylamino) phenol hydrochloride (114) as a white solid (1.37 g, 51%).

(114) (1.35 g, 0.057 mmol) and triethylamine (1.17 g, 1.61 $cm^3$, 0.114 mol) in toluene (15 $cm^3$) was slowly added, over 15 minutes, to a refluxing solution of p-nitrophenyl chloroformate (115) (1 g, 0.005 mol) in toluene (15 $cm^3$) and the mixture refluxed for one hour. After this time, the reaction was cooled, concentrated in vacuo and purified by column chromatography (silica, dichloromethane) to give the diester, carbonic acid-p-(bis-2-chloroethylamino)phenyl ester-p-nitrophenyl ester (PNMC) (116) as a yellow oil (1.27 g, 64%) which solidified upon standing.

To a solution of nitrophenyl carbonate (116) (1.35 g, 0.057 mmol) in chloroform (1 $cm^3$) was added L-tyrosine methyl ester (117) (0.127 g, 0.65 mmol) and the mixture refluxed for four hours. After this time, the reaction was cooled and concentrated in vacuo. Column chromatography gave prodrug 2.1.1 as a colourless oil (0.085 g, 62%).

Example 4

Synthesis of 1.1.5 (3-Acetyl-3,5,12-trihydroxy-1-[5-hydroxy-4-(4-hydroxyphenylaminocarbonylamino)-6-methylperhydro-2-pyranoloxy]10-methoxy-(1S,3S)-1,2,3,4,6,11-hexaydro-6,11-napthac nedione)

The synthesis of 1.1.5 is shown in Scheme 4. Tyramine (119) (1 g, 7.3 mmol) and p-nitrophenylchloroformate (120) (1.4 g, 7.3 mmol) were dissolved in anhydrous dichloromethane and heated under reflux for 2 hours. The reaction mixture was allowed to cool, concentrated in vacuo and purified by dry flash column chromatography (silica, dichloromethane and then ethylacetate) to afford carbamate (121) as a pale yellow solid (2.2 g, 97%); m.p. 157–159° C.; $v_{max}$ (KBr disc) 400, 1658, 1440, 1380/$cm^{-1}$; δ $^1$H (400 MHz, CDCl3) 2.74 (2H, t, J 7.0 Hz, CH2Ar), 3.4 (2H, t, J7.0 Hz, CH2) 6.76 (2H, d, J8 Hz, 2×ArH), 8.24 (2H, d, J9.2 Hz, ArH); δ $^{13}$C(100 MHz, CDCl$_3$); 36.4 (CH$_2$), 44.2 (CH$_2$), 116.6 (2×CH), 123.7 (2×CH), 26.4(2×CH), 131.2 (2×CH), 131.3 (C) 146.9 (C), 156.0 (C), 157.4 (C), 158.1 (C). m/z (Cl) 162 (25%), 139 (10), 107 (100) 65 (15).

Daunomycin (122) (20 mg, 0.038 mmol) and carbamate (121) (15 mg, 0.49 mmol) were dissolved in dimethylformamide (1 mL) and diisopropylethylamine (7.5 μL, 0.042 mmol) was added. The flask was wrapped in tinfoil to exclude light and the mixture was stirred for 3 hours. Diethyl ether (5 mL) was added to give a red precipitate. The precipitate was collected by filtering across a cotton wool plug. The solid was then washed off the cotton wool using methanol (5 mL) and concentrated in vacuo to yield prodrug 1.1.5 as a red oily solid (12 mg, 46%). $v_{max}$ 3400, 2720, 1740, 1750, 1690, 1520, 1435, 1147/cm$^{-1}$; $\delta^1$H (400 MHz, CD$_3$OD) 1.25 (2H, d, J 4.5 Hz, CH$_2$), 1.32–1.4 (5H, m, 5' CH$_3$ and CH$_2$CCOH$_3$), 1.72–1.89 (2H, m 2'CH$_2$), 2.35 (3H, s, COCH$_3$), 2.55 (2H, t, J 3.72 Hz, ArCH$_2$CH$_2$N), 3.54–3.55 (1H, m, 4'CHOH), 3.71 (1H, m, C(CHO)CH$_2$), 3.83 (3H, s, ArOCH$_3$), 3.92 (1H, brd, 1'CH), 4.25 (1H, q, J 3.8 Hz, 5'CH), 5.31–5.33 (1H, m, 3'CH), 6.58 (2H, d, J 5.6 Hz, 2×ArH), 6.91 (2H, d, J 5.6 Hz, 2×ArH), 7,27 (1H, t, J 3.3 Hz, ArH), 7.55–7.57 (2H, m, 2×ArH; $\delta^{13}$C (100 MHz, CD$_3$OD) 25.1 (CH$_3$), 31.2 (CH), 32.0 (CH$_2$), 33.9 (CH$_2$), 37.0 (CH$_2$), 43.2 (CH$_2$), 44.2 (CH$_2$), 47.6 (CH) 56.2 (CH), 57.4 (CH), 69.1 (CH), 74.3 (CH$_3$) 77.9 (C), 80.0 (CH3) 102.7 (CH), 131.1 (3×CH), 131.8 (CH), 135.9 (2×C), 136.2 (2×C), 136.3 (2×C), 137.4 (2×CH), 156.4 (C), 157.2 (C), 157.7 (2×C), 160.6 (2×C), 187.6 (C), 187.9 (C), 214.1 (C); m/z (Cl) 383 (20%), 363 (100), 347 (15), 293 [urea linked tyramine to 4-OH-5-Me-hexose(15)], 174 (10), 138 (10), 107 (10), 74 (10).

Examples 5

Carbonic acid-p-(bis-2-chloroethylamino)phenyl ester-p-nitrophenyl ester (PNMC) (6).

Benzyl-p-(bis-2-hydroxyethylamino)phenyl ether (3).

4-Benzyloxyaniline hydrobromide (11.8 g, 0.05 mol) was suspended in glacial acetic acid (70 mL) and water (70 mL) and cooled to 0° C. Ethylene oxide (17.64 g, 20 cm$^3$, 0.4 mol) was then added, in 1 mL portions, the solution allowed to warm to room temperature and stirred until no starting material remained by TLC. Additional ethylene oxide was added as required in order to drive the reaction to completion. After this time, the solution was concentrated in vacuo (T<60° C.) to give a red/brown syrup, which was re-dissolved in chloroform (100 mL). This solution was washed with water (50 mL) and saturated sodium bicarbonate solution (50 mL), dried (magnesium sulfate), filtered and concentrated in vacuo. Re-crystallisation (toluene/hexane) gave the diol as a pale cream powder (12.55 g, 88%); m.p. 96–7° C. (lit.[5] 93–4° C.); R$_f$ (silica, ethyl acetate) 0.3; $\delta^1$H (400 MHz, CDCl$_3$) 3.71–3.82 (8H, br m. 4×CH$_2$), 6.79 (2H, br d., J 8.6 Hz, PhCH$_2$), 7.39 (2H, br d., J 8.6 Hz, Ph), 7.41–7.55 (7H, m, Ar).

Benzyl-p-(bis-2-chloroethylamino)phenyl ether (4).

The bis-(hydroxyethylamino)phenyl ether 3 (2.0 g, 7.2 mmol) was dissolved in anhydrous pyridine (11 mL) and cooled to 0° C. Mesyl chloride (28.8 mmol, 2.23 mL) was added and the solution stirred at 2–4° C. for 20 minutes, followed by heating at 80° C. for 30 minutes. Ethyl acetate (30 mL) and water (30 mL) were then added, the organic fraction collected, dried (magnesium sulfate), filtered and concentrated in vacuo. Column chromatography (silica gel, dichloromethane) gave the dichloride (1.38 g, 59%) as a white powder, m.p. 108–09° C. (lit.[6] 105–06° C.); R$_f$ 0.7 (silica, dichloromethane); $\delta^1$H (400 MHz, CDCl$_3$) 3.16–3.27 (8H, m, 4×CH$_2$), 5.00 (2H, s, PhCH$_2$), 6.73 (2H, d, J 8.6 Hz, Ph), 6.92 (2H, d, J 8.6 Hz, Ar), 7.29–7.44 (5H, m, Ar).

p-(Bis-2-chloroethylamino)phenol hydrochloride (5).

Hydrogen chloride gas was bubbled through a solution of the bis-(chloroethylamino)phenyl ether 4 (3.3 g, 0.01 mol) in methanol (35 mL), until complete dissolution occurred. Filtration and concentration in vacuo gave the hydrochloride salt as a white powder {m.p. 140–41° C. (lit[7] 135–36° C.)}, which was immediately re-suspended in ethanol (40 mL) containing 10% palladium on carbon (0.17 g). The suspension was stirred under an atmosphere of hydrogen until no starting material remained (TLC). The suspension was then filtered over celite and concentrated in vacuo to give the phenol hydrochloride as a white solid (1.37 g, 51%); m.p. 176–78° C. (170–73° C.); $\delta$ $^1$H (400 MHz, CDCl$_3$, free amine) 3.52–3.63 (8H, m, 4×CH$_2$), 6.57 (2H, d, J 9.0 Hz, Ar), 6.67 (2H, d, J 9.0 Hz, Ar).

Carbonic acid-p-(bis-2-chloroethylamino)phenyl ester-p-nitrophenyl ester (PNMC) (6).

The bis-chloroethylamino hydrochloride salt 5 (1.35 g, 5.79 mmol) and triethylamine (1.17 g, 1.61 mL, 11.4 mmol) in toluene (15 mL) was slowly added, over 15 minutes, to a refluxing solution of p-nitrophenylchloroformate (1 g, 4.96 mmol) in toluene (15 mL) and the mixture was heated under reflux for one hour. After this time, the reaction was cooled, concentrated in vacuo and purified by column chromatography (silica gel, dichloromethane) to give the diester as a yellow oil (1.27 g, 64%) which solidified upon standing; m.p. 97–99° C.; R$_f$ 0.77 (silica, dichloromethane); $v_{max}$ (KBr disc) 1767, 1615, 1594, 1512, 1347, 1180, 814/cm$^{-1}$; $\delta$ $^1$H (400 MHz, CDCl$_3$) 3.61–3.68 (4H, m, 2×CH$_2$), 3.71–3.88 (4H, m, 2×CH$_2$), 6.70 (2H, d, J 9.2 Hz, Ar), 7.16 (2H, d, J 9.2 Hz, Ar), 7.47 (2H, d, J 9.1 Hz, Ar), 8.30 (2H, d, J 9.1 Hz, Ar); $\delta^{13}$C (100 MHz, CDCl$_3$) 40.2 (CH$_2$), 53.6 (CH$_2$), 112.4 (CH), 121.7 (CH), 121.8 (CH), 125.3 (CH), 140.5 (C), 141.3 (C), 142.7 (C), 143.1 (C), 153.6 (C); (Cl: found: 399.0525 [M+H]$^+$. C$_{17}$H$_{16}$Cl$_2$N$_2$O$_5$ [M+H]$^+$, requires 399.0514); m/z (Cl) (399 [M+H]$^+$, 75%), 348 (100), 120 (20), 63 (15).

Example 6

{2'-(4"-Hydroxyphenyl)ethyl} carbamic acid p-(bis-2-chloroethylamino)phenyl ster (9).

To a solution of the nitrophenyl carbonate 6 (0.20 g, 0.57 mmol) in chloroform (1 mL) was added tyramine hydrochloride (0.096 g, 0.50 mmol) and triethylamine (0.50 g, 0.08 mL, 0.50 mmol) and the mixture was heated under reflux for four hours. After this time, the reaction was cooled, concentrated in vacuo and purified by column chromatography (silica gel, dichloromethane:ethyl acetate 95:5) to give the carbamate 9 as a colourless oil (0.046 mg, 47%); R$_f$ 0.29 (silica, dichloromethane:ethyl acetate 95:5); $\square_{max}$ (KBr disc) 3336, 1718, 1612, 1507, 1336, 1219/cm$^{-1}$; $\delta$ $^1$H (400 MHz, CDCl$_3$) 2.80 (2H, t, J 6.9 Hz, PhCH$_2$), 3.47 (2H, apparent dd, J 6.9 Hz, 6.0 Hz, CH$_2$NH), 3.61 (2H, d, J 6.0 Hz, 2×NCH), 3.68 (4H, d, J 6.0 Hz, 2×CH$_2$Cl), 6.67 (1H, br t, J 6.0 Hz, NH), 6.67 (2H, d, J 9.0 Hz, Ar), 6.77 (2H, d, J 8.4 Hz, Ar), 6.99 (2H, d, J 9.0 Hz, Ar), 7.03 (2H, d, J 8.4 Hz, Ar); $\delta^{13}$C (100 MHz, CDCl$_3$); 35.3 (CH$_2$), 40.5 (CH$_2$), 42.8 (CH$_2$), 54.3 (CH$_2$), 113.4 (CH), 115.8 (CH), 123.1 (CH), 130.2 (CH), 130.7 (C), 143.6 (C), 154.7(C), 155.8 (C and CO); (Cl: found: 397.1085 [M+H]$^+$. C$_{19}$H$_{22}$Cl$_2$N$_2$O$_3$ requires 397.1085); m/z (Cl) (397 [M+H]$^+$, 45%), 234 (100), 184 (95), 107 (100).

Example 7

{2'-(3",4"-Dihydroxyphenyl)-ethyl} carbamic acid p-(bis-2-chloroethylamino) phenyl ester (10).

A solution of the carbonate 6 (0.1 g 0.26 mmol), 3-hydroxytyramine hydrochloride (0.1 g, 0.53 mmol) and triethylamine (0.05 g, 0.07 mL, 0.5 mmol) in anhydrous dimethylformamide (1.5 mL) was stirred for three days at ambient temperature. After this time, the mixture was concentrated to dryness in vacuo. Column chromatography (silica gel, dichloromethane:methanol 100:1→9:1 v/v) gave the carbamate 10 as a colourless viscous oil (0.08 g, 73%); $R_f$ 0.45 (silica, dichloromethane:methanol, 9:1, v/v); $\nu_{max}$ (KBr disc) 3421, 1718, 1653, 1507, 1218 cm$^{-1}$; δ $^1$H(400 MHz, CDCl$_3$) 2.60 (2H, br t, J 6.3 Hz, PhCH$_2$), 3.32 (2H, br q, J 6.3 Hz, CH$_2$NH), 3.48 (4H, d, J 6.2 Hz, 2×NCH$_2$), 3.55 (4H, d, J 6.2 Hz, 2×CH$_2$Cl), 5.17 (1H, br t, J 6.3 Hz, NH), 6.50 (2H, d, J 7.9 Hz, Ar), 6.58 (2H, s, Ar), 6.64 (1H, d, J 7.7 Hz, Ar), 6.88 (2H, d, J 7.9 Hz, Ar); δ$^{13}$C (100 MHz, CDCl$_3$) 35.3 (CH$_2$), 40.7 (CH$_2$), 42.7 (CH$_2$), 53.9 (CH$_2$), 112.8 (CH), 115.6 (CH), 116.8 (CH), 120.9 (CH), 123.0 (CH), 130.9 (C), 142.5 (C), 143.0 (C), 144.1 (C), 144.4 (C), 156.1 (C and CO); (Cl: found: [M+H]$^+$, 413.1045. C$_{19}$H$_{22}$Cl$_2$N$_2$O$_4$ requires 413.1034); m/z (Cl) 413 ([M+H]$^+$, 10%), 233 (50), 184 (100), 123 (35).

Example 8

(R)-[2'-Amino-3'-(4"-hydroxyphenyl)propionic acid methyl ester]-carbamic acid p-(bis-2-chloroethylamino) phenyl ester (12).

To a solution of the nitrophenyl carbonate 6 (0.20 g, 0.57 mmol) in chloroform (1 mL) was added L-tyrosine methyl ester (0.127 g, 0.65 mmol) and the mixture was heated under reflux for four hours. After this time, the reaction was cooled and concentrated in vacuo. Column chromatography (silica gel, dichloromethane:methanol 100:1) afforded carbamate 12 as a colourless oil (0.085 g, 62%); $R_f$ 0.16 (silica, dichloromehane:ethyl acetate 95:5); $[\alpha]_D^{20}$ +29.0° (c 0.9, chloroform); $\nu_{max}$ (KBr disc) 3446, 1718, 1700, 1559, 1496, 1218/cm$^{-1}$; δ $^1$H (400 MHz, CDCl$_3$) 3.03 (2H, dq, J 5.9 Hz, 14.2 Hz PhCH$_2$), 3.54 (2H, d, J 6.2 Hz, 2×NCH$_2$), 3.68 (2H, d, J 6.0 Hz, 2×CH$_2$Cl), 3.69 (3H, s, Me), 4.58 (2H, br d, J 6.6 Hz, CH), 5.41 (1H, d, J 8.0 Hz, NH), 6.61 (2H, d, J 9.0 Hz, Ar), 6.68 (2H, d, J 8.4 Hz, Ar), 6.92 (2H, d, J 9.1 Hz, Ar), 6.94 (2H, d, J 9.1 Hz, Ar); δ$^{13}$C (100 MHz, CDCl$_3$); 37.3 (CH$_2$), 40.3 (CH$_2$), 52.4 (CH$_3$), 53.7 (CH$_2$), 55.0 (CH), 112.6 (CH), 115.5 (CH), 122.7 (CH) 127.2 (C), 130.3 (CH), 142.3 (C), 143.8 (C), 154.7 (C), 155.0 (C), 172.0 (C); (Cl: found: 455.1148 [M+H]$^+$. C$_{21}$H$_{24}$Cl$_2$N$_2$O$_5$ requires 455.1141); m/z (Cl) (455 [M+H]$^+$, 10%), 234 (15), 184 (35), 107 (100).

Example 9

3',4'-Dihydroxybenzylamino-carbamic acid p-(bis-2-chloroethylamino) phenyl ester (15).

A solution of carbonate 6 (0.13 9, 0.32 mmol), 3,4-dihydroxybenzylamine hydrobromide (0.14 g, 0.65 mmol) and triethylamine (0.07 g, 0.09 mL, 0.65 mmol) in anhydrous dimethylformamide (2 cm$^3$) was stirred at room temperature for 72 hours. After this time, the mixture was concentrated to dryness in vacuo. Column chromatography (silica gel, dichloromethane:methanol 100:1→9:1 v/v) gave carbamate 15 as a white powder (0.07 g, 52%); $R_f$ 0.29 (silica, dichloromethane: methanol, 9:1, v/v); $\nu_{max}$ (KBr disc) 3322, 1689, 1616, 1507, 1427, 1281, 1215, 1037/cm$^{-1}$; δ $^1$H (400 MHz, CD$_3$OD) 3.65 (4H, d, J 6.2 Hz, 2×NCH$_2$), 3.71 (4H, d, J 6.2 Hz, 2×CH$_2$Cl), 4.17 (2H, br d, J 7.3 Hz, CH$_2$), 6.64 (1H, br t, J 7.3 Hz, NH), 6.74–6.81 (5H, m, Ar), 6.96 (2H, d, J 7.4 Hz, Ar); δ$^{13}$C (100 MHz, CD$_3$OD) 41.6 (CH$_2$), 45.3 (CH$_2$), 54.6 (CH$_2$), 113.9 (CH), 115.7 (CH), 116.2 (CH), 119.9 (CH), 123.7 (CH), 144.0 (C), 145.4 (C), 145.6 (C), 146.3 (C), 158.0 (C and CO); (Cl: found: [M+H]$^+$, 399.0870. C$_{18}$H$_{20}$Cl$_2$N$_2$O$_4$ requires 399.0878); m/z (Cl) ([M+H]$^+$, 20%), 363 (10), 233 (70), 184 (100).

Example 10

(R)-[1'-Amino-2'-(3,4'-hydroxyphenyl)ethanonic acid methyl ester]-carbamic acid p-(bis-2-chloroethylamino) phenyl ester (16).

(R)-3,4-Hydroxyphenylglycine methyl ester (14). To a stirred solution of 3,4-hydroxyphenylglycine (0.5 g, 3.0 mmol) in 2,2-dimethoxypropane (30 mL) was added concentrated hydrochloric acid (3 mL). After stirring overnight at 20° C., the mixture was concentrated to dryness in vacuo, and minimal methanol added to re-dissolve the residues. Diethyl ether (75 mL) was added and the resultant solid obtained by filtration. Re-dissolution in methanol (30 mL) and addition of triethylamine (0.3 g, 0.4 mL, 3 mmol), followed by concentration in vacuo and column chromatography (silica gel, dichloromethane:methanol 20:1 v/v) gave the free amine 14 as a white powder in quantitative yield; m.p. 172–73° C. (lit.[8] 178–80° C.); $[\alpha]_D^{20}$ –114.4° (c 0.25, 10% aq. hydrochloric acid) {lit.[9] $[\alpha]_D^{20}$ –121.1° (c 1, aq. hydrochloric acid)}; $R_f$ 0.55 (silica, dichloromethane:methanol, 10:1, v/v); $\nu_{max}$ (KBr disc) 3447, 1734, 1559, 1517, 1465, 1281, 1255, 1220, 1167/cm$^{-1}$; δ $^1$H (400 MHz, CDCl$_3$) 3.24 (2H, br s, NH$_2$), 3.60 (3H, s, Me), 4.46 (1H, br s., CH), 6.70 (2H, d, J 8.6 Hz, Ar), 7.07 (2H, d, J 8.6 Hz, Ar); δ$^{13}$C (100 MHz, CDCl$_3$) 55.1 (CH), 61.3 (CH$_3$), 118.9 (CH), 131.7 (CH), 134.0 (C), 161.0 (C), 178.2 (C); (Cl: found: [M+H]$^+$, 182.0822. C$_9$H$_{11}$NO$_3$ requires 182.0818); m/z (Cl) 182 ([M+H]$^+$, 15%), 165 (50), 122 (100), 107 (5).

(R)-[1'-Amino-2'-(3,4"-hydroxyphenyl)ethanonic acid methyl ester]-carbamic acid p-(bis-2-chloroethylamino) phenyl ester (16).

A solution of the carbonate 6 (0.13 g, 0.32 mmol) and the amino acid methyl ester 14 (0.14 g, 0.65 mmol) in anhydrous dimethylformamide (2 mL) was stirred at room temperature for 72 hours. After this time, the mixture was concentrated to dryness in vacuo. Column chromatography (silica gel, dichloromethane:ethyl acetate, 95:5, v/v) gave carbamate 16 as a colourless viscous oil (0.07 g, 54%); $[\alpha]^{p20}$ –115.8° (c 0.85, chloroform); $R_f$ 0.14 (silica, dichloromethane:ethyl acetate, 95:5, v/v); $\nu_{max}$ (KBr disc) 3384, 1718, 1612, 1506, 1437, 1350, 1218, 1174, 1030/cm$^{-1}$; δ $^1$H (400 MHz, CDCl$_3$) 3.17 (3H, s, OMe), 3.48 (4H, d, J 6.2 Hz, 2×NCH$_2$), 3.57 (4H, d, J 6.2 Hz, 2×CH$_2$Cl), 5.23 (1H, d, J 7.0 Hz, NH), 6.08 (1H, d, J 7.0 Hz, CH), 6.52 (2H, d, J 8.0 Hz, Ar), 6.61 (2H, d, J 7.7 Hz, Ar), 6.90 (2H, d, J 7.7 Hz, Ar), 7.10 (2H, d, J 8.0 Hz, Ar); δ$^{13}$C (100 MHz, CDCl$_3$) 40.3 (CH$_2$), 52.9 (CH$_3$), 53.6 (CH$_2$), 57.4 (CH), 112.5 (CH), 115.8 (C), 122.6 (CH), 127.6 (C), 128.4 (CH), 142.1 (C), 143.8 (C), 154.5 (C), 156.4 (C), 171.5 (C); (Cl: found: [M+H]$^+$, 441.0968. C$_{20}$H$_{22}$Cl$_2$N$_2$O$_5$ requires [M +H]$^+$, 441.0984); m/z (Cl) 441 ([M+H]$^+$, 10%), 277 (10), 233 (35), 184 (70), 147 (100).

Example 11

(R)-[1'-Amino-2'-hydroxy-2'-(4"-hydroxyphenyl)proplonic acid methyl ester]-carbamic acid p-(bis-2-chloroethylamino) phenyl ester (18).

A solution of the carbonate 6 (0.13 9, 0.32 mmol) and L-adrenaline (0.12 g, 0.65 mmol) in anhydrous dimethylformamide (2 mL) was stirred at room temperature for 72 hours. After this time, the mixture was concentrated to dryness in vacuo. Column chromatography (silica gel, dichloromethane:methanol 100:1→9:1 v/v) gave carbamate 18 as a viscous colourless oil (0.06 g, 44%); $[\alpha]_D^{20}$ −21.9° (c 0.95, chloroform); $R_f$ 0.29 (silica, dichloromethane:methanol, 9:1, v/v); $\nu_{max}$ (KBr disc) 3368, 1700, 1611, 1516, 1448, 1357, 121, 1219/cm$^{-1}$; δ $^1$H (400 MHz, CDCl$_3$) 3.41 (2H, d, J 7.4 Hz, CH$_2$), 3.52 (3H, s, Me), 3.53 (4H, d, J 6.2 Hz, 2×NCH$_2$), 3.64 (4H d, J 6.2 Hz, 2×CH$_2$Cl), 4.81 (1H, d, J 7.4 Hz, CH), 6.57–6.92 (7H, m, Ar); δ$^{13}$C (100 MHz, CDCl$_3$) 34.7 (CH$_3$), 36.3 (CH$_2$), 40.4 (CH$_2$), 53.6 (CH$_2$), 72.5 (CH), 112.5 (CH), 113.1 (CH), 115.2 (CH), 118.2 (CH), 122.7 (CH), 133.5 (C), 142.5 (CH), 143.9 (C), 144.0 (C), 157.2 (C and CO); (Cl: found: [M+H]$^+$, 443.1079. C$_{20}$H$_{24}$Cl$_2$N$_2$O$_5$ requires 443.1140); m/z (Cl) 443 ([M+H]$_+$, 20%), 425 (100), 234 (70),184 (100), 184 (85), 121 (20).

Example 12

{2'-(4''-Hydroxyphenyl)ethylamine) carbamic acid p-(bis-2-chloroethylamino) phenyl ester (21).

2-(4-Hydroxyphenoxy)-ethylamine hydrochloride (19).[10]

A solution of 4-hydroxyacetamide 34 (1.45 g, 8.8 mmol) in anhydrous tetrahydrofuran (63 mL) was slowly added under an inert atmosphere to a refluxing suspension of lithium aluminium hydride (1M soln. in anhydrous tetrahydrofuran, 32 mL) and the suspension refluxed for a further 12 hours. After cooling, water was slowly added until hydrogen evolution ceased and the mixture concentrated in vacuo. After re-suspension in methanol, the mixture was eluted through a short pad of silica with methanol and the organic extracts concentrated in vacuo, re-dissolved in concentrated hydrochloric acid and re-concentrated in vacuo to give the amine hydrochloride as a white powder (0.2 g, 12%); m.p. 170–71° C. (lit.[10] 172–74° C. dec.); $^1$H (250 MHz, D$_2$O) δ 3.25 (2H, t, J 5.2 Hz, CH$_2$), 4.08 (2H, t, J 5.2 Hz, CH$_2$), 6.73 (2H, d, J 9.1 Hz, Ar), 6.82 (2H, d, J 9.1 Hz, Ar).

2-[(4-hydroxyphenyl)thio]ethylamine hydrochloride (20).

A mixture of 4-hydroxythiophenol (2.48 g, 19.7 mmol) and 2-methyl-2-oxazoline (1.67 g, 1.69 mL, 19.7 mmol) were refluxed (neat) under argon for two hours. Upon cooling, the crude sticky solid was re-suspended in concentrated hydrochloric acid (aq) and refluxed for 12 hours. The mixture was then poured into water (20 mL) and extracted with diethyl ether (2×20 mL). The aqueous liquors were concentrated to dryness and twice re-dissolved in water and re-concentrated. Re-crystallisation of the resultant solid (ethanol:diethyl ether) gave the product as a cream solid (0.45 g, 11%); m.p. 130–31 ° C. (lit.[11] 128–29° C.); $^1$H (400 MHz, D$_2$O) δ 3.07 (4H, br s, 2×CH$_2$), 6.87 (2H, d, J 11.9 Hz, Ar), 7.41 (2H, d, J 11.9 Hz, Ar)

{2'-(4''-Hydroxyphenyl)ethylamine} carbamic acid p-(bis-2-chloroethylamino) phenyl ester (21).

A solution of 19 (0.2 g, 1 mmol), 6 (0.3 g, 0.75 mmol) and triethylamine (0.1 g, 0.14 mL, 1 mmol) in anhydrous chloroform (3 mL) was heated under reflux under an inert atmosphere for 4 hours and concentrated in vacuo. Column chromatography (silica gel, ethyl acetate:dichloromethane 1:19 v/v) gave carbamate 21 as a colourless oil (0.11 g, 27%); $R_f$ 0.26 (silica, ethyl acetate:dichloromethane 1:19 v/v); $\nu_{max}$ (KBr disc) 3358, 1713, 1612, 1506, 1452, 1337, 1217, 1109, 1068, 826/cm$^{-1}$; δ $^1$H (250 MHz, CDCl$_3$) 3.47 (4H, d, J 7.8 Hz, 2×CH$_2$), 3.56 (2H, t, J 5.0 Hz, CH$_2$), 3.65 (4H, d, J 7.8 Hz, 2×CH$_2$), 3.91 (2H, t, J 5.0 Hz, CH$_2$). 5.55 (1H, t, J 5.8 Hz, NH), 6.53 (2H, d, J 9.1 Hz, Ar), 6.67 (4H, d, J 1.4 Hz, Ar), 6.90 (2H, d, J 9.1 Hz, Ar); δ$^{13}$C (62.8 MHz, CDCl$_3$) 40.7 (CH$_2$), 41.3 (CH$_2$), 54.1 (CH$_2$), 67.6 (CH$_2$), 112.9 (CH), 115.9 (CH), 116.5 (CH), 123.2 (CH), 142.7 (C), 144.2 (C), 150.7 (C), 152.6 (C), 156.2 (C and CO); (Cl: found: [M+H]$^+$, 413.1049. C$_{19}$H$_{22}$N$_2$O$_4$ requires 413.1034); m/z (Cl) 413 ([M+H]$^+$, 15%), 234 (70), 184 (100), 135 (10), 110 (55), 65 (15).

Example 13

2'-[(4''-Hydroxyphenyl)thio]ethylamine} carbamic acid p-(bis-2-chloroethylamino) phenyl ester (22).

A solution of 20 (0.2 g, 1 mmol) and triethylamine (0.1 g, 0.14 mL, 1 mmol) in anhydrous chloroform (3 mL) was brought to reflux and 6 (0.3 g, 0.75 mmol) added. After refluxing under an inert atmosphere for 4 hours and concentration in vacuo, column chromatography (silica gel, ethyl acetate:dichloromethane 1:19 v/v) gave carbamate 22 as a colourless oil (0.16 g, 39%); $R_f$ 0.34 (silica, ethyl acetate:dichloromethane 1:19 v/v); $\nu_{max}$ (KBr disc) 3333, 1700, 1651, 1612, 1556, 1495, 1455, 1397, 1335, 1266, 1218, 1182, 1110, 1048/cm$^{-1}$; δ $_1^{13}$H (250 MHz, CDCl$_3$) 2.88 (2H, d, J 6.3 Hz CH$_2$), 3.34 (2H, q, J 6.3 Hz, CH$_2$), 3.51 (4H, d, J Hz, 2×CH$_2$), 3.58 (4H, d, J Hz, 2×CH$_2$), 5.44 (1H, t, J 6.0 Hz, NH), 6.57 (2H, d, J 9.1 Hz, Ar), 6.64 (2H, d, J 11.7 Hz, Ar), 6.91 (2H, d, J 9.1 Hz, Ar), 7.20 (2H, d, J 11.7 Hz, Ar); δ$^{13}$C (62.8 MHz, CDCl$_3$) 36.1 (CH$_2$), 40.5 (CH$_2$), 40.7 (CH$_2$), 54.0 (CH$_2$), 112.9 (CH), 116.7 (CH), 123.1 (CH), 126.4 (CH), 134.5 (CH), 142.6 (C), 144.3 (C), 156.1 (C), 156.4 (C and CO).

Example 14

2'-(4''-hydroxyphenyl)ethyl} thiocarbamic acid p-(bis-2-chloroethylamino)phenyl ester (25).

A solution of the mustard 5 (0.2 g, 0.86 mmol) and methylamine (0.174 g, 0.24 mL, 1.72 mmol) was slowly added to a refluxing solution of pentafluorophenylchlorothionoformate in toluene (3 mL) and the mixture was heated under reflux for two hours. After this time, the reaction was cooled and concentrated in vacuo. The resultant product and tyrosine methyl ester (0.336 g, 1.72 mmol) were then dissolved in anhydrous dimethylformamide (5 mL) and stirred under an inert atmosphere at ambient temperature overnight. After this time the reaction was concentrated in vacuo and purified by column chromatography (silica gel, dichloromethane:ethyl acetate 95:5) to give thiocarbamate 25 as a colourless oil (0.30 g, 68%); $[\alpha]_D^{20}$ +53.4° (c 2.3, chloroform); $R_f$ 0.42 (silica, dichloromethane:ethyl acetate 95:5); $\nu_{max}$ (KBr disc) 3400, 1737, 1614, 1507, 1444, 1378, 1147/cm$^{-1}$; δ $^1$H (400 MHz, CDCl$_3$) 3.16 (1H, dd, J 13.2 Hz, 4.8 Hz, CH$_2$CH), 3.31 (1H, dd, J 14.3 Hz, 5.5 Hz, CH$_2$CH), 3.62 (4H, t, J 5.8 Hz, 2×NCH$_2$), 3.69 (4H, t, J 5.8 Hz, 2×CH$_2$Cl), 3.77 (3H, s, OMe), 5.16 (1H, dd, J 13.2 Hz, 5.5 Hz, CH), 5.56 (1H, br s, NH), 6.63 (2H, d, J 8.8 Hz, Ar), 6.77 (2H, d, J 7.9 Hz, Ar), 6.96 (2H, d, J 8.8 Hz, Ar), 6.99 (2H, d, J 7.9 Hz, Ar); δ$^{13}$C (100 MHz, CDCl$_3$); 36.1 (CH$_2$), 40.3 (CH$_2$), 52.6 (CH$_3$), 52.7 (CH$_2$), 58.9 (CH), 112.0 (CH), 115.6 (CH), 123.5 (CH), 127.0 (C), 130.4 (CH), 144.2 (C), 144.4 (C), 154.9 (C), 171.4 (C), 189.8.

Example 15 bis-(2-Chloroethyl)amino-4-hydroxyphenylaminomethanone (28).

di-(2-Chloroethyl)amino4-nitrophenoxymethanone (27).

Bis-(2-chloroethylamine) hydrochloride (5.6 mmol, 1 g) and p-nitrophenylchloroformate (5.4 mmol, 1 g) were dissolved in dimethylformamide (15 mL) and triethylamine (11.5 mmol, 1.6 mL) was added slowly. The mixture was heated under reflux with stirring for 6 hours before being concentrated in vacuo to give a brown oil. Purification by column chromatography (silica gel, dichloromethane) yielded carbamate 27 as a yellow oil (1.2 g, 70%). $v_{max}$ 1660, 1446, 1378,1145/cm$^{-1}$; δ $^1$H (400 MHz CDCl$_3$) 1.21–1.33 (4H, m, CH$_2$), 3.38–3.47 (4H, m, CH$_2$), 7.51 (2H, d, J 5.7 Hz, 2×ArH), 8.32 (2H, d, J 5.7 Hz, 2×ArH); $δ^{13}$C (100 MHz, CDCl$_3$) 30.8 (CH$_2$), 42.1 (CH$_2$), 44.4 (CH$_2$), 44.7 (CH$_2$), 115.9 (2×CH), 131.2 (2×CH), 129.3 (C), 157.6 (C), 160.5 (C). m/z (Cl) 273 (65%), 150 (50), 134 (100), 100 (10), 56 (25).

Example 16 bis-(2-Chloroethyl)amino-4-hydroxyphenylaminomethanone (28). 27 (860 mg, 2.8 mmol) was dissolved in dimethylformamide (20 mL) and triethylamine (0.9 mL, 5.6 mmol) was added. The mixture was stirred at reflux for 30 minutes and tyramine (0.76 mg, 5.6 mmol) was added. The mixture was heated under reflux for a further 6 hours and then concentrated in vacuo. Purification by column chromatography (silica gel, dichloromethane then methanol) gave prodrug 28 as an orange/brown oil (571 mg, 67%). $v_{max}$ 3400, 1660, 1444, 1380, 1145/cm$^{-1}$; δ $^1$H (400 MHz, CDCl$_3$) 2.61 (2H, t, J 3.72 Hz, 4CH$_2$Ar), 3.17–3.22 (10H, m, ArCH$_2$CH$_2$, 2×CH$_2$CH$_2$Cl), 6.67 (2H, d, J 5.7 Hz, 2×ArH), 6.9 (2H, d, J 5.7 Hz, 2×ArH), 7.82 (1H, brs, NH); $δ^{13}$C (100 MHz, CDCl$_3$), 30.1 (CH$_2$), 43.1 (CH$_2$), 43.4 (CH$_2$), 44.2 (CH$_2$), 46.2 (CH$_2$), 46.7 (CH$_2$), 115.9 (2×CH), 130 (2×CH), 130.1 (C), 155.6 (C), 161.5 (C). m/z (Cl) 269 (87%), 224 (50), 138 (100), 121 (45), 108 (35).

Example 17 bis-(2-Chloroethyl)amino-4-hydroxyphenylaminomethanone (28). One pot method. bis-(2-Chloroethyl)amine hydrochloride 26 (200 mg, 1.1 mmol) was dissolved in dichloromethane (15 mL) and triethylamine (0.45 mL, 3.3 mmol) was added. The mixture was stirred for 5 minutes at ambient temperature and ethyl chloroformate or methyl chlorothioformate (1.32 mmol) was added. The mixture was stirred until no bis-(2-chloroethyl)amine remained by TLC (ethyl acetate). Tyramine (300 mg, 2.2 mmol) was added and the mixture was heated under reflux for 4 hours. the mixture was allowed to cool, purified by dry flash column chromatography (silica gel, dichloromethane 200 cm$^3$) and concentrated in vacuo to yield prodrug 28 as an orange/brown oil (234 mg, 67% for methyl chlorothioformate and 229 mg, 64% for ethyl chloroformate).

Example 18 di-(2-Chloroethyl)amino4-hydroxyphenethyl(methyl) aminomethanone (29). bis-(2-Chloroethyl)amine hydrochloride 26 (200 mg, 1.1 mmol) was dissolved in dichloromethane (15 mL) and triethylamine (0.45 mL, 3.3 mmol) was added. The mixture was stirred for 5 minutes at ambient temperature and methyl chlorothioformate (1.32 mmol) was added. The mixture was stirred until no bis-(2-chloroethyl) amine remained by TLC (ethyl acetate). N-mehty tyramine (322 mg, 2.1 mmol) was added and the mixture was heated under reflux for 4 hours. The mixture was allowed to cool, purified by dry flash column chromatography (silica gel, dichloromethane 200 mL) and concentrated in vacuo to yield prodrug 29 as an orange/brown oil (68 mg, 18%). $v_{max}$ 3400, 1660, 1444, 1380, 1145/cm$^{-1}$; δ $^1$H (400 MHz, CDCl$_3$) 2.32 (3H, s, CH$_3$) 2.60 (2H, t, J 3.72 Hz, CH$_2$Ar), 3.17–3.22 (10H, m, ArCH$_{2CH2}$, 2×CH$_2$CH$_2$Cl), 6.67 (2H, d, J 5.7 Hz, 2×ArH), 6.9 (2H, d, J 5.7 Hz, 2×ArH), 7.82 (1H, brs, NH); $δ^{13}$C (100 MHz, CDCl$_3$) 30.1 (CH$_2$), 43.3 (CH$_2$), 44.1 (CH$_2$), 44.2 (CH$_2$), 45.2 (CH$_2$), 46.5 (CH$_3$) 46.6 (CH$_2$), 115.9 (2×CH), 130 (2×CH), 130.1 (C), 155.6 (C), 161.5 (C). m/z (Cl) 283 (87%), 238 (50) 152 (100), 121 (45), 108 (35).

Example 19

Methyl-2-di(2chloroethyl)aminocarbonylamino-3-(4-hydroxyphenyl)proponoate (30). bis-(2-Chloroethyl)amine hydrochloride 26 (200 mg, 1.1 mmol) was dissolved in dichloromethane (15 mL) and triethylamine (0.45 mL, 3.3 mmol) was added. The mixture was stirred for 5 minutes at ambient temperature and methyl chlorothioformate (1.32 mmol) was added. The mixture was stirred until no bis-(2-chloroethyl)amine remained by TLC (ethyl acetate). Tyrosine methyl ester (411 mg, 2.1 mmol) was added and the mixture was heated under reflux for 4 hours. The mixture was allowed to cool purified by dry flash column chromatography (silica gel, dichloromethane 200 mL) and concentrated in vacuo to yield prodrug 30 as an orange/brown oil (278 mg, 60%). $v_{max}$ 3400, 1740, 1660, 1444, 1380, 1145/cm$^{-1}$; δ $^1$H (400 MHz, CDCl$_3$) 2.32 (3H, s, CH$_3$) 2.60 (2H, t, J 3.72 Hz, CH$_2$Ar), 2.64 (3H, s, CH$_3$) 3.12–3.25 (9H, m, ArCH$_2$CH, 2×CH$_2$CH$_2$Cl), 6.67 (2H, d, J 5.7 Hz, 2×ArH), 6.9 (2H, d, J 5.7 Hz, 2×ArH), 7.82 (1H, brs, NH);. $δ^{13}$C (100 MHz, CDCl$_3$) 29.8 (CH$_2$), 43.3 (CH$_2$), 44.1 (CH$_2$), 44.2 (CH$_2$), 45.2 (CH$_2$), 46.6 (CH$_2$), 47.1 (CH$_3$) 115.9 (2×CH), 130 (2×CH), 130.1 (C), 155.6 (C), 160.3 (C) 161.5 (C). m/z (Cl) 242 (72%), 227 (45), 183 (75) 152 (100), 121 (45), 108 (35).

Example 20

3-Acetyl-3,5,12-trihydroxy-1-[5-hydroxy-4-(4-hydroxyphenylaminocarbonylamino)-6-methylperhydro-2-pyranoloxy]-10-methoxy-(1S,3S)-1,2,3,4,6,11-hexahydro-6,11-naphthacenedione (32).

4-Hydroxyphenethylamino-4-nitrophenoxymethanone (31). Tyramine (1 g, 7.3 mmol) and p-nitrophenylchloroformate (1.4 g, 7.3 mmol) were dissolved in anhydrous dichloromethane and heated under reflux for 2 hours. The reaction mixture was allowed to cool, concentrated in vacuo and purified by dry flash column chromatography (silica, dichloromethane and then ethylacetate) to afford carbamate 31 as a pale yellow solid (2.2 g, 97%); m.p. 157–159° C.; $v_{max}$ (KBr disc) 3400, 1658, 1440, 1380/cm−1; δ $^1$H (400 MHz, CDCl$_3$) 2.74 (2H, t, J 7.0 Hz, CH$_2$Ar), 3.4 (2H, t, J 7.0 Hz, CH$_2$) 6.76 (2H, d, J 8.5 Hz, 2×ArH), 7.06 (2H, d, J 8.5 Hz, 2×ArH), 7.29 (2H, d, J 9.2 Hz, 2×ArH), 8.24 (2H, d, J 9.2 Hz, ArH); $δ^{13}$C (100 MHz, CDCl$_3$); 36.4 (CH$_2$), 44.2 (CH$_2$), 116.6 (2×CH), 123.7 (2×CH), 126.4 (2×CH), 131.2 (2×CH), 131.3 (C) 146.9 (C), 156.0 (C), 157.4 (C), 158.1 (C). m/z (Cl) 163 (25%), 139 (10), 107 (100) 65 (15).

3-Acetyl-3,5,12-trihydroxy-1-[5-hydroxy-4-(4-hydroxyphenylaminocarbonylamino)-6-methylperhydro-2-pyranoloxy]-10-methoxy-(1S,3S)-1,2,3,4,6,11-hexaydro-6,11-naphthacenedione (32).

Daunomyodin[12] (20 mg, 0.038 mmol) and carbamate 31 (15 mg, 0.049 mmol) were dissolved in dimethylformamide (1 mL) and diisopropylethylamine (7.5 µL, 0.042 mmol) was added. The flask was wrapped in tinfoil to exclude light and the mixture was stirred. for 3 hours. Diethyl ether (5 mL) was added to give a red precipitate. The precipitate was collected by filtering across a cotton wool plug. The solid was then washed off the cotton wool using methanol (5 mL) and concentrated in vacuo to yield prodrug 32 as a red oily solid (12 mg, 46%). $v_{max}$ 3400, 2720, 1740, 1750, 1690, 1520, 1435, 1147/cm$^{-1}$; δ $^1$H (400 MHz, CD$_3$OD) 1.25 (2H, d, J4.5 Hz, C$\underline{H}_2$), 1.32–1.4 (5H, m, 5' CH$_3$ and C$\underline{H}_2$CCOCH$_3$), 1.72–1.89 (2H, m, 2'CH$_2$), 2.35 (3H, s, COCH$_3$), 2.55 (2H, t, J 3.72 Hz, ArC$\underline{H}_2$CH$_2$N), 3.18 (2H, t, J 3.72 Hz, ArCH$_2$C$\underline{H}_2$N), 3.54–3.55 (1H, m, 4'C$\underline{H}$OH), 3.71 (1H, m, C(C$\underline{H}$O)CH$_2$), 3.83 (3H, s, ArOCH$_3$), 3.92 (1H, brd, 1'CH), 4.25 (1H, q, J 3.8 Hz, 5'CH), 5.31–5.33 (1H, m, 3'CH), 6.58 (2H, d, J 5.6 Hz, 2×ArH), 6.91 (2H, d, J 5.6 Hz, 2×ArH), 7.27 (1H, t, J 3.3 Hz, ArH), 7.55–7.57 (2H, m, 2×ArH); δ$^{13}$C (100 MHz, CD$_3$OD) 25.1 (CH$_3$), 31.2 (CH), 32.0 (CH$_2$), 33.9 (CH$_2$), 37.0 (CH$_2$), 43.2 (CH$_2$), 44.2 (CH$_2$), 47.6 (CH) 56.2 (CH), 57.4 (CH), 69.1 (CH), 74.3 (CH$_3$) 77.9 (C), 80.0 (CH$_3$) 102.7 (CH), 131.1 (3×CH), 131.8 (CH), 135.9 (2×C), 136.2 (2×C), 136.3 (2×C), 137.4 (2×CH), 156.4 (C), 157.2 (C), 157.7 (2×C), 160.6 (2×C), 187.6 (C), 187.9 (C), 214.1 (C); m/z (CI) 383 (20%), 363 (100), 347 (15), 293 [urea linked tyramine to 4-OH-5-Me-hexose(15)], 174 (10), 138 (10), 107 (10), 74 (10).

Example 21

In Vitro Tests

The stability of compounds according to the invention was assessed in the following experiments.

Tests were run under cell-line conditions, that is, in RPMI 1640, fetal bovine serum, and L-glutamine at 37° C., and the percentage decomposition was measured over time. The compounds tested represented different linkages between the therapeutically active agent and the part of the molecule recognised by tyrosinase (i.e. carbamate linked, thiocarbamate linked, urea linked) and different therapeutically active agents (i.e. normustine, phenol-mustard, daunomycin and taxol derivatives). As well as structure 1.1.2 given above, the structures tested were:

1.1.1

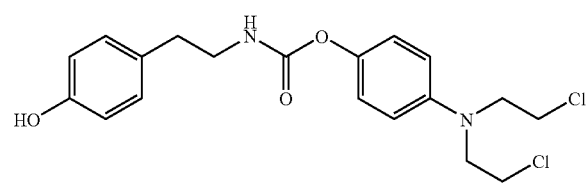

2.2.1

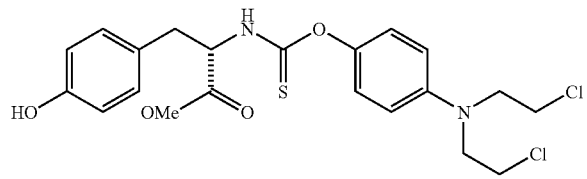

1.1.5

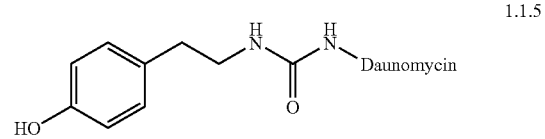

The results were as follows:

| | % decomposition over time | | | | | | | |
|---|---|---|---|---|---|---|---|---|
| Drug | 1 hr | 2 hrs | 3 hrs | 4 hrs | 6 hrs | 12 hrs | 24 hrs | 48 hrs |
| 1.1.2 | 0 | 0 | 0 | 0 | 0 | 0 | 0 | 0 |
| 1.1.5 | 0 | 0 | 0 | 0 | 0 | 0 | 0 | 0 |
| 1.1.1 | 7 | 44 | 61 | 74 | 100 | — | — | — |
| 2.2.1 | 52 | 92 | 100 | — | — | — | — | — |

The results showed that compounds according to the invention having a urea linkage were more stable than compounds possessing a carbamate linkage.

This test shows that the most stable linkage is a urea linkage. The urea-linked prodrugs (1.1.2 and 1.1.5) showed no decomposition over a two-day test period. The carbamate-linked prodrug (1.1.1) was less stable in fetal bovine serum, and exhibited a half-life of approximately 2.5 hrs. The thiocarbamate-linked prodrug (2.1.1) decomposed the most rapidly, with a half-life of approximately 1.5 hrs.

Example 22

Oximetry

When tyrosinase substrates are oxidised according to the pathway in Scheme 1, molecular oxygen is absorbed from the surrounding solution. The resulting oxygen depletion can be measured using an oxygen sensor, thereby oxygen uptake is a measure of the rate of tyrosinase oxidation of the prodrugs. Using this technique we were able to examine the oxidation of the prodrugs by tyrosinase (Table 2). The relative rates of oxygen uptake were used to estimate the efficiency of the prodrugs to act as tyrosinase substrates. In order to obtain a quantitative comparison of tyrosinase-catalysed oxidation of our prodrugs we also examined the rate of oxygen uptake in the presence of the methyl ester of the natural substrate tyrosine (entry 14, table 2).

FIG. 1 is a graph of the oxidation rate of prodrugs by mushroom tyrosinase. FIG. 1 shows that prodrug 28 bis-(2-chloroethylamino)-4-hydroxyphenylamino-methanone was an excellent tyrosinase substrate ($R_{max}$= 20 nanomoles/min). This is further demonstrated by comparing oxygen depletion in the oximetry cuvettes of prodrug 28 and tyrosine methyl ester over 400 seconds, which shows that the brief lag period is shortened in the case of the oxidation of the prodrug. (see FIG. 2). Prodrugs 9, 10 and 30 were also good substrates, exhibiting similar oxidation rates to tyrosine methyl ester. Hetercatom Incorporation (oxygen or sulfur) to afford pro-durgs 21 and 22 resulted in slower oxidation. For example, the oxidation rate was only 7.5 nanomoles/min for prodrug 21 and 22.

Figure 2:
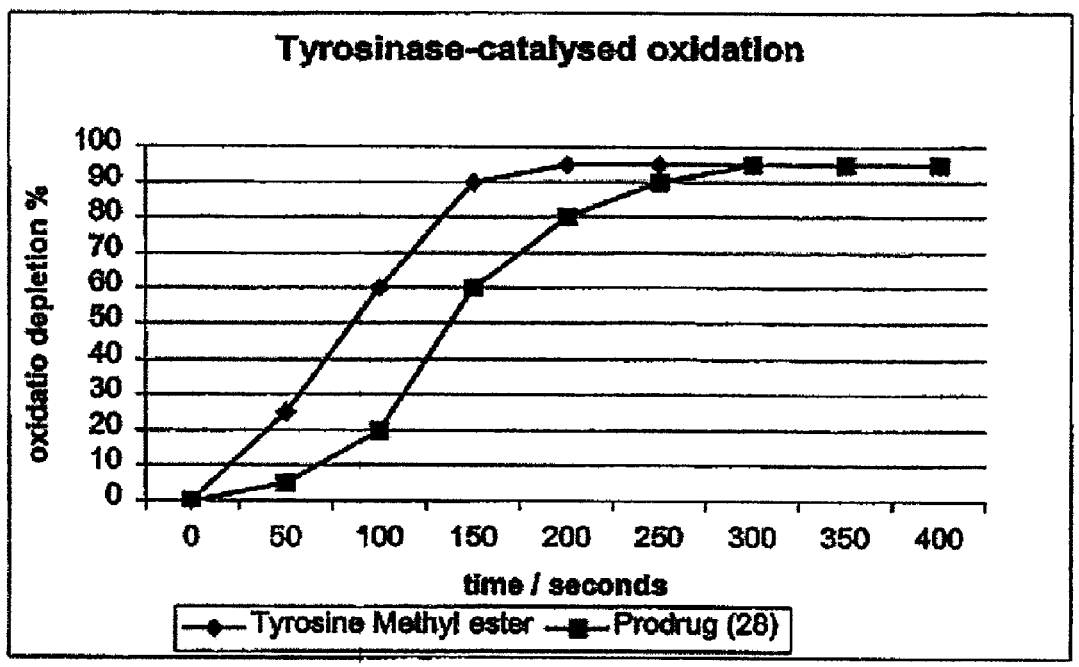

FIG. 2 is a graph of tyrosinase oxidation of tyrosine methyl ester and prodrug 28. The results of the oximetry study highlight the structural properties that diminish oxidation rate. For example, prodrug 16 was not oxidized by tryorinase within a 15 minutes incubation period. We conclude that, shortening the dopamine chain lenght from two carbons to one carbon resulted in reduced affinity to the enzyme. This may be due to increased steric hindrance close to the active site of the enzyme. Nitrogen methylation also resulted in a reduced rate of oxidation (prodrug 29), suggesting the importance of a primary or secondary amine function. Not surprisingly, the sterically hindered daunomycin-based prodrug 32 was also a poor substrate with an $R_{max}$ of only 5 nanomles/min.

The results of the oximetry study highlight the structural properties that diminish oxidation rate. For example, prodrug 16 was not oxidised by tyrosinase within a 15 minutes incubation period. We conclude that, shortening the dopamine chain length from two carbons to one carbon resulted in reduced affinity to the enzyme. This may be due to increased steric hindrance close to the active site of the enzyme. Nitrogen methylation also resulted in a reduced rate of oxidation (prodrug 29), suggesting the importance of a primary or secondary amine function. Not surprisingly, the sterically hindered daunomycin-based prodrug 32 was also a poor substrate with an $R_{max}$ of only 5 nanomoles/min.

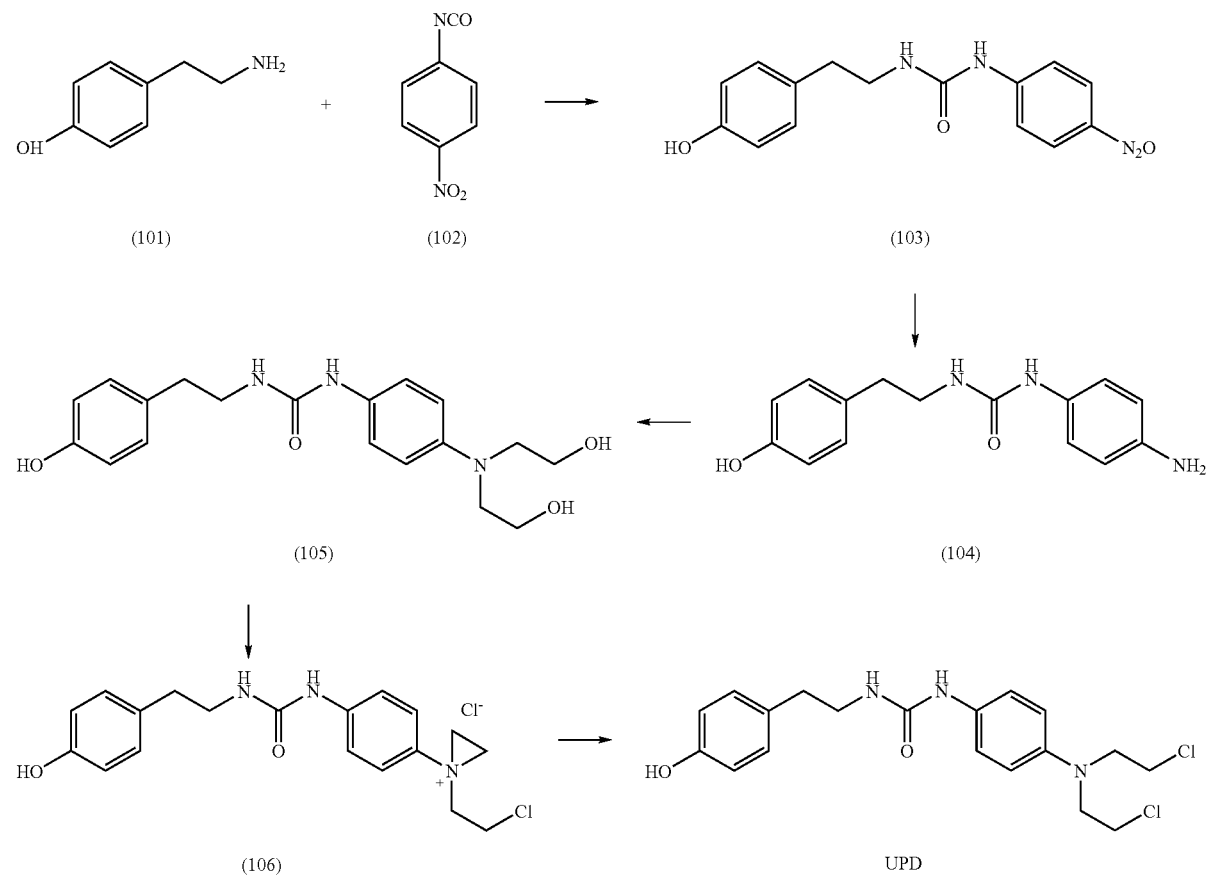

SCHEME 1
SYNTHESIS OF UPD

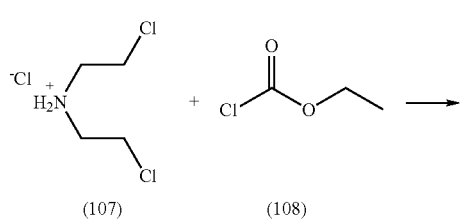

SCHEME 2
SYNTHESIS OF 1.1.2

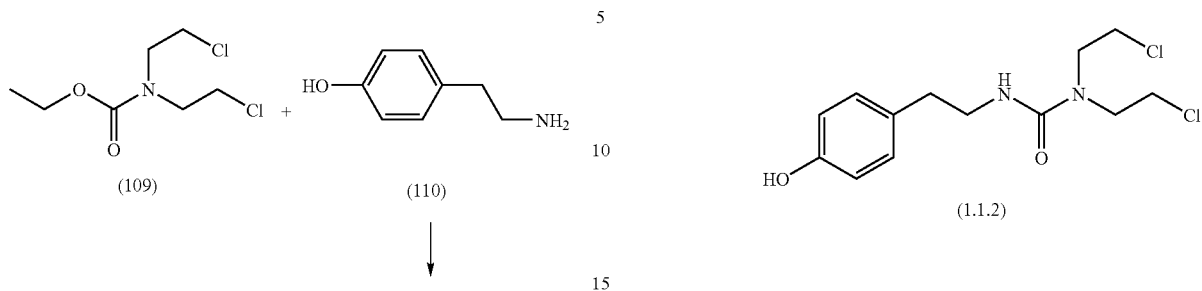
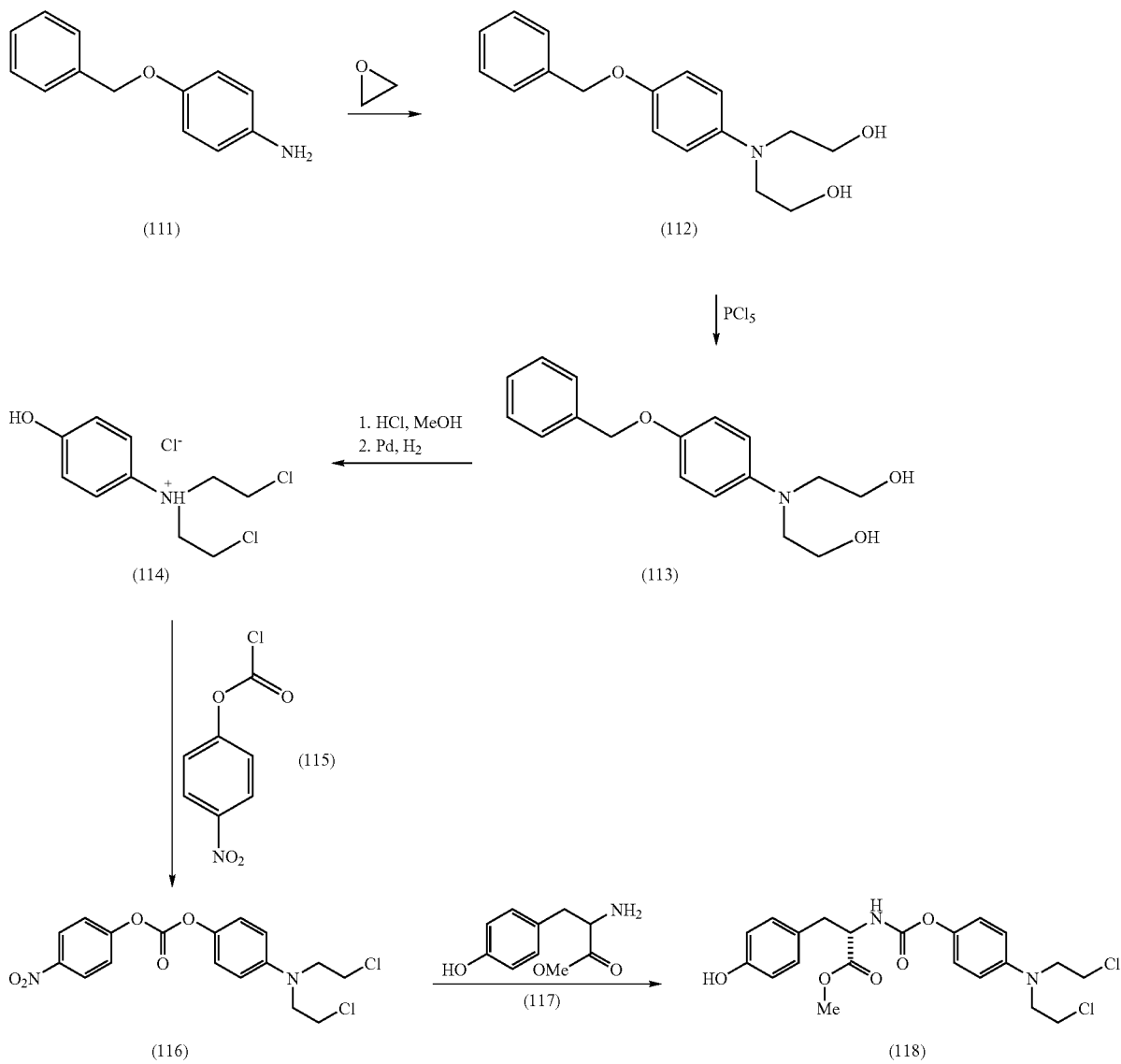
SCHEME 3
SYNTHESIS OF 2.1.1

SCHEME 4
SYNTHESIS OF 1.1.5

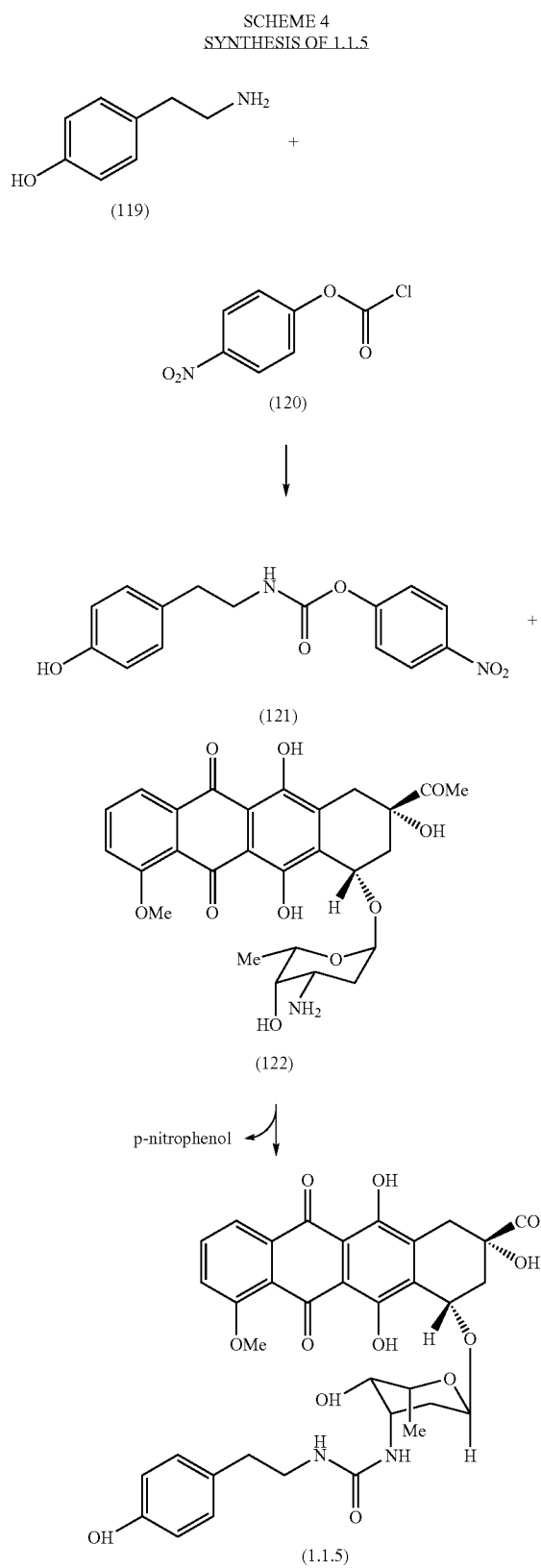

1. A. M. Jordan, T. H. Khan, H. M. I. Osborn, A Photiou, P. A. Riley, *Biorg. Med. Chem,* 1999, 7, 1775.

2. M. H. Benn, A. M. Creighton, L. N. Owen, G. R. White, *J. Chem. Soc,* 1961, 2365.

3. T. Nakagawa, K. Ueno, M. Kashtwa, J. Wantanabe, *Tetrahedron Lett.,* 1194, 35, 1921.

4. K. A. Jorgensen, A.-B. A. G. Ghattas, S. -O. Lawesson, *Tetrahedron,* 1982, 38, 1163

5. M. H. Benn, A. M. Creighton, L. N. Owen, G. R. White, *J. Chem. Soc.,* 1961, 2365

6. T. Nakagawa, K. Ueno, M. Kashiwa, J. Wantanabe, *Tetrahedron Lett.,* 1994, 35, 1921

7. M. Artico, C. J. Ross, *Biochem. Pharmacol.,* 1968, 17, 893

8. J. C. Clark, *J. Chem. Soc. Perkin Trans.* 1, 1976, 475

9. E. P. Kyba, *J. Amer. Chem. Soc.,* 1978, 100, 4555

10. W. Kandatege, M. W. Sheldon, *J. Ame. Chem. Soc.,* 1987, 109, 4036

11. S. R. Padgette, H. H. Herman, J. H. Han, S. H. Pollock, S. W. May, *J. Med. Chem.,* 1984, 27, 1354

The invention claimed is:

1. A compound having the formula (Ia), (Ib) or (Ic), or a pharmaceutically acceptable salt thereof:

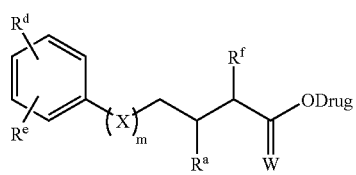

Ia

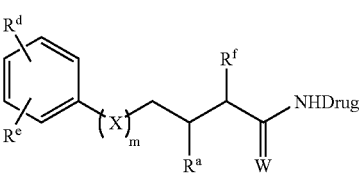

Ib

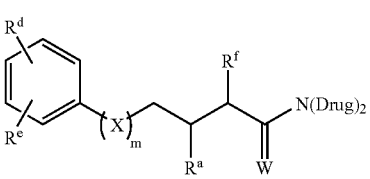

Ic wherein $R^a$ is hydrogen or —$COOR^b$, $R^b$ is hydrogen or $C_{1-6}$ alkyl; $R^d$ and $R^e$ independently represent hydrogen and hydroxy, $R^f$ is hydrogen, $C_{1-4}$ alkyl or halogen, X is —CHOH—, —$CH_2$—oxygen or sulphur, m is zero or 1, W is oxygen or sulphur, and —ODrug is selected from:

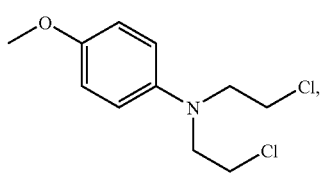

a residue of taxol or gemcitabine;
—NHDrug is selected from:

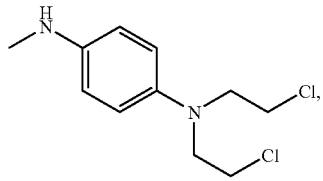

or a residue of daunomycin;
and —N(Drug)₂ is:

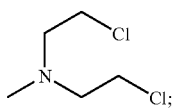

and with the provisos (1) that where said compound has general formula (Ia) wherein m is zero, W represents oxygen, $R^d$ is hydrogen and $R^e$ is hydroxyl in the para position, and $R^a$ represents —COOMe, —ODrug does not represent a residue of digoxin, and (2) that where said compound has general formula (Ib) wherein m is zero, W represents oxygen and $R^d$ is hydrogen, $R^e$ is hydroxyl in the para position.

2. A compound according to claim 1 wherein $R^d$ represents m-hydroxy and $R^e$ represents p-hydroxy.

3. A compound according to claim 1 wherein $R^d$ represents hydrogen and $R^e$ represents p-hydroxy.

4. A compound according to claim 1 wherein m is zero.

5. A compound according to claim 1 wherein $R^f$ is hydrogen.

6. A compound according to claim 1 wherein W represents oxygen.

7. A method of treating melanoma in a patient which comprises administering a compound having the formula (Ia), (Ib) or (Ic), or a pharmaceutically acceptable salt thereof:

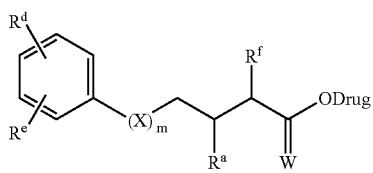

Ia

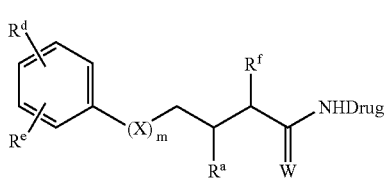

Ib

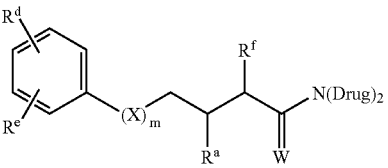

Ic wherein $R^a$ is hydrogen or —COOR$^b$, $R^b$ is hydrogen or $C_{1-6}$ alkyl; $R^d$ and $R^e$ independently represent hydrogen and hydroxy, $R^f$ is hydrogen, $C_{1-4}$ alkyl or halogen, X is —CHOH—, —CH2—oxygen or sulphur, m is zero or 1, W is oxygen or sulphur, and —ODrug is selected from:

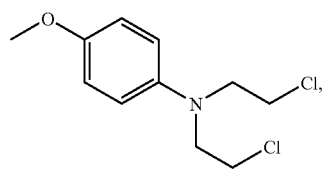

a residue of taxol or gemcitabine;
—NHDrug is selected from:

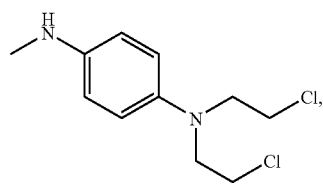

or a residue of daunomycin;
and —N(Drug)₂ is:

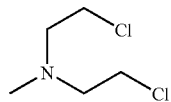

* * * * *